(12) United States Patent
Hibbard

(10) Patent No.: US 11,992,702 B2
(45) Date of Patent: May 28, 2024

(54) MACHINE LEARNING OPTIMIZATION OF FLUENCE MAPS FOR RADIOTHERAPY TREATMENT

(71) Applicant: Elekta, Inc., Atlanta, GA (US)

(72) Inventor: Lyndon Stanley Hibbard, St. Louis, MO (US)

(73) Assignee: Elekta, Inc., Atlanta, GA (US)

( * ) Notice: Subject to any disclaimer, the term of this patent is extended or adjusted under 35 U.S.C. 154(b) by 496 days.

(21) Appl. No.: 16/948,486

(22) Filed: Sep. 21, 2020

(65) Prior Publication Data
US 2022/0088410 A1 Mar. 24, 2022

(51) Int. Cl.
*A61N 5/10* (2006.01)
*G06N 3/08* (2023.01)

(52) U.S. Cl.
CPC ......... *A61N 5/1031* (2013.01); *A61N 5/1038* (2013.01); *A61N 5/1045* (2013.01); *A61N 5/1081* (2013.01); *G06N 3/08* (2013.01)

(58) Field of Classification Search
CPC ........ A61N 5/10; A61N 5/103; A61N 5/1031; A61N 5/1038; A61N 5/1045; A61N 5/1081; A61N 2005/1041; A61N 5/1082; A61N 5/1047; A61N 5/1042; A61N 5/1043; A61N 5/1044; A61N 5/1037; A61N 5/1039; G06N 3/08
See application file for complete search history.

(56) References Cited

U.S. PATENT DOCUMENTS

| | | |
|---|---|---|
| 2008/0298550 A1 | 12/2008 | Otto |
| 2013/0142310 A1 | 6/2013 | Fahimian et al. |
| 2016/0129282 A1 | 5/2016 | Yin et al. |
| 2016/0140300 A1 | 5/2016 | Purdie et al. |
| 2017/0177812 A1 | 6/2017 | Sjolund |
| 2018/0154179 A1 | 6/2018 | Ollila et al. |

(Continued)

FOREIGN PATENT DOCUMENTS

| | | |
|---|---|---|
| CN | 109843377 | 6/2019 |
| CN | 110944717 | 3/2020 |

(Continued)

OTHER PUBLICATIONS

"International Application Serial No. PCT US2021 071408, International Search Report dated Jan. 5, 2022", 4 pgs.

(Continued)

*Primary Examiner* — Devin B Henson
*Assistant Examiner* — Evelyn Grace Park
(74) *Attorney, Agent, or Firm* — Schwegman Lundberg & Woessner, P.A.

(57) ABSTRACT

Systems and methods are disclosed for generating fluence maps for a radiotherapy treatment plan that uses machine learning prediction. The systems and methods include identifying image data that indicates treatment constraints for target dose areas and organs at risk areas in an anatomy of the subject, generating anatomy projection images that represent a view of the subject from respective beam angles, using a trained neural network model to generate the computer-simulated fluence map representations based on the anatomy projection images, where the fluence maps indicate a fluence distribution of the radiotherapy treatment at each of the beam angles.

35 Claims, 24 Drawing Sheets

(56) References Cited

U.S. PATENT DOCUMENTS

| | | | |
|---|---|---|---|
| 2018/0185672 | A1 | 7/2018 | Ramezanzadeh Moghadam |
| 2018/0310907 | A1* | 11/2018 | Zhang .................. G06F 3/0346 |
| 2019/0030370 | A1 | 1/2019 | Hibbard |
| 2019/0051398 | A1* | 2/2019 | Zankowski ............ G06N 20/00 |
| 2019/0192880 | A1 | 6/2019 | Hibbard |
| 2019/0318474 | A1 | 10/2019 | Han |
| 2019/0333623 | A1 | 10/2019 | Hibbard |
| 2020/0111194 | A1* | 4/2020 | Wang ..................... G06N 3/045 |
| 2021/0192809 | A1* | 6/2021 | Paysan ................. G06T 11/006 |
| 2022/0008748 | A1* | 1/2022 | Huang ................. A61N 5/1031 |

FOREIGN PATENT DOCUMENTS

| | | |
|---|---|---|
| CN | 116391234 | 7/2023 |
| WO | 2014205128 | 12/2014 |
| WO | 2015193776 | 12/2015 |
| WO | 2016023786 | 2/2016 |
| WO | 2016081916 | 5/2016 |
| WO | 2018048575 | 3/2018 |
| WO | 2019023142 | 1/2019 |
| WO | 2019212804 | 11/2019 |
| WO | WO-2020256750 A1 | 12/2020 |
| WO | 2022061324 | 3/2022 |
| WO | WO-20222711971 A1 | 12/2022 |

OTHER PUBLICATIONS

"International Application Serial No. PCT US2021 071408, Written Opinion dated Jan. 5, 2022", 4 pgs.

"Ray Tracing (graphics)", Wikipedia https://en.wikipedia.org/wiki/Ray_tracing_(graphics), (2019), 15 pgs.

Appenzoller, Lindsey M., et al., "Predicting dose-volume histograms for organs-at-risk in IMRT planning", Medical physics 39.12, (2012), 7446-7461.

Babier, A, et al., "Knowledge-based automated planning with three-dimensional generative adversarial networks", Medical Physics, (Dec. 21, 2018), 15 pgs.

Bishop, Christopher M., "Pattern Recognition and Machine Learning", Chapter 2-Probability Distributions In Publication of Information Science and Statistics, Springer, (2006), 72 pgs.

Breedveld, S., et al., "A novel approach to multi-criteria inverse planning for IMRT", Phys Med Biol, 52, (2007), 6339-6353.

Breedveld, S., et al., "Fast, multiple optimzations of quadratic dose objective functions in IMRT", Phys Med Biol, 51, (2006), 3569-3579.

Breedveld, S., et al., "iCycle: Integrated, multicriterial beam angle, and profile optimization for generation of coplanar and noncoplananr IMRT plans", Med Phys, 39(2), (2012), 951-963.

Breedveld, Sebastiaan, et al., "The equivalence of multi-criteria methods for radiotherapy plan optimization", Physics in Medicine & Biology 54.23, (2009), 7199-7209.

Glassner, A S, "An Introduction to Ray Tracing", Morgan-Kauffman Part 1 out of 2, (1989), 177 pgs.

Goodfellow, Ian, et al., "Deep Learning", The MIT Press, 2016, vol. 1, ISBN 978-0-262-03561-3, (2016), 63 pages.

Goodfellow, Ian, et al., "Generative Adversarial Nets", Advances in Neural Information Processing Systems 27, Curran Associates, Inc., (Jun. 10, 2014), 9 pgs.

Isola, Phillip, et al., "Image-to-Image Translation with Conditional Adversarial Networks", arXiv:1611.07004 [cs.CV], (Nov. 22, 17), 17 pgs.

Johnson, Hans J, et al., "The ITK Software Guide", (Jul. 25, 2019), 997 pgs.

Kak, A C, et al., "Principles of Computerized Tomographic Imagining Chapter 3", SIAM Philadephia, (2001), 64 pgs.

Krizhevsky, Alex, et al., "Imagenet classification with deep convolutional neural networks", Advances in neural information processing systems, (2012), 9 pgs.

Lecun, Yann, et al., "Deep learning", Nature, vol. 521. 7553, (2015), 436-444.

Mcintosh, C, et al., "Contextual Atlas Regression Forests: Multiple-Atlas-Based Automated Dose Prediction in Radiation Therapy", IEEE Transactions on Medical Imaging, (2016), 15 pgs.

Murphy, Kevin P, "Machine Learning A Probabilistic Perspective", MIT Press, Cambridge, Ma, USA Part 2 out of 2, (2012), 549 pgs.

Nguyen, D, et al., "A feasibility study for predicting optimal radiation therapy dose distributions of prostate cancer patients from patient anatomy using deep learning", Scientific Reports www.nature.com/scientificreports, (Jan. 31, 2019), 10 pgs.

Rit, S, et al., "The Reconstruction Toolkit (RTK), an open-source cone-beam CT reconstruction toolkit based on the Insight Toolkit (ITK)", (2013), 5 pgs.

Romeijn, Edwin H, et al., "A unifying framework for multi-criteria fluence map optimization models", Phys. Med. Biol. 49 (2004), (May 4, 2004), pp. 1991-2013.

Ronneberger, Olaf, et al., "U-Net Convolutional Networks for Biomedical Image Segmentation", Computer Science Department and BIOSS Centre for Biological Signalling Studies, University of Freiburg, Germany, (May 18, 2015), 234-241.

Shirashi, S, et al., "Knowledge-based prediction of three-dimensional dose distributions for external beam radiotherapy", Medical Physics, 43(1), (2015), 378-287.

Shirley, P, et al., "Fundamentals of Computer Graphics", Chapter 10 Ray Tracing AK Peters, (2005), 785 pgs.

Unkelbach, Jan, et al., "Optimization approaches to volumetric modulated arc therapy planning", Am. Assoc. Phys. Med. 42 (3), (Mar. 2015), 12 pgs.

Voet, PWJ, et al., "Fully automated volumetric modulated arc therapy plan generation for prostate cancer patients", IJROBP, 88(5), (2014), 1175-1179.

Voet, PWJ, et al., "Integrated multicriterial optimization of beam angles and intensity profiles for coplanar and noncoplanar head and neck IMRT and implications for VMAT", Med Phys, 39(8), (2012), 4858-4865.

Wachowicz, K, et al., "On the direct acquisition of beam's-eye-view images in MRI for integration with external beam radiotherapy", Physics in Medicine, (2018), 11 pgs.

Wang, Y., et al., "Evaluation of plan quality assurance models for prostate cancer patients based on fully automatically generated Pareto-optimal treatment plans", Phys Med Biol, 61, (2016), 4268-4282.

Wu, B., et al., "Patient geometry-driven information retrieval for IMRT treatment plan quality control", Medical Physics, 36(12), (2009), 5497-5505.

Zarepisheh, Masoud, et al., "A multicriteria framework with voxel dependent parameters for radiotherapy treatment plan optimization", Am. Assoc. Phys. Med.41 (4), (Apr. 2014), 11 pgs.

Zhu, J.-Y., et al., "Unpaired Image-to-Image Translation using Cycle-Consistent Adversarial Networks", arXiv:1703.10593v1 [cs.CV], (Mar. 30, 2017).

Zhu, X., et al., "A planning quality evaluation tool for prostate adaptive IMRT based on machine learning", Medical Physics, 38(2), (2011), 719-726.

"International Application Serial No. PCT US2017 046608, International Search Report dated Jan. 15, 2018", 6 pgs.

"International Application Serial No. PCT US2017 046608, Written Opinion dated Jan. 15, 2018", 6 pgs.

"International Application Serial No. PCT US2017 046608, Invitation to Pay Add'l Fees and Partial Search Report dated Nov. 8, 2017", 7 pages.

"Conditional Generative Adversarial Nets in TensorFlow", Agustinus Kristiadi's Blog, [Online]. Retrieved from the Internet: URL: https: wiseodd.github.io techblog 2016 12 24 conditional-gan-tensorflow, 6 pgs.

"International Application Serial No. PCT US2018 043320, International Search Report dated Oct. 29, 2018", 6 pgs.

"International Application Serial No. PCT US2018 043320, Written Opinion dated Oct. 29, 2018", 7 pgs.

"Imagenet", Stanford University Vision Lab, Accessed from Internet on Nov. 9, 2018 http: www.image-net.org , (2016), 1 pg.

"International Application Serial No. PCT US2017 046608, International Preliminary Report on Patentability dated Mar. 21, 2019", 8 pgs.

(56) References Cited

OTHER PUBLICATIONS

"Australian Application Serial No. 2017324627, First Examination Report dated Jun. 11, 2019", 4 pgs.
"Australian Application Serial No. 2017324627, Response filed Jul. 17, 2019 to First Examination Report dated Jun. 11, 2019", 22 pgs.
"Australian Application Serial No. 2017324627, Subsequent Examiners Report dated Sep. 11, 2019", 11 pgs.
"International Application Serial No. PCT US2019 028720, International Search Report dated Oct. 16, 2019", 4 pgs.
"International Application Serial No. PCT US2019 028720, Written Opinion dated Oct. 16, 2019", 8 pgs.
"International Application Serial No. PCT US2018 043320, International Preliminary Report on Patentability dated Feb. 6, 2020", 9 pgs.
"Beam's Eye View", Wikipedia https: en.wikipedia.org wiki Beam%27s_eye_view, (Accessed on mar. 13, 2020), 1 pg.
"European Application Serial No. 17755011.8, Office Action dated Jan. 14, 2020", 3 pgs.
"International Application Serial No. PCT US2019 039830, International Search Report dated Mar. 13, 2020", 4 pgs.
"European Application Serial No. 17755011.8, Response to Communication pursuant to Rules 161(1) and 162 EPC filed Mar. 20, 2020", 10 pgs.
"U.S. Appl. No. 16/784,919, Notice of Allowance dated Apr. 15, 2021", 10 pgs.
"U.S. Appl. No. 16/784,919, Corrected Notice of Allowability dated May 19, 2021", 4 pgs.
Androsova, E E, "Application of recursive recurrent neural networks", New information technologies in automated systems (with English translation), (2016), 18 pages.
Bukovsky, Ivo, "A Fast Neural Network Approach to Predict Lung Tumor Motion during Respiration for Radiation Therapy Applications", BioMed Research International vol. 2015, Article ID 489679, (2015), 3 pgs.
Chris, McIntosh, "Fully automated treatment planning for head and neck radiotherapy using a voxel-based dose prediction and dose mimicking method", Physics in Medicine and Biology, vol. 62, No. 15, XP055416743, (Sep. 2, 2016), 5926-5944.
Creswell, Antonia, "Generative Adversarial Networks: An Overview", IEEE Signal Processing Magazine 35.1, (2018), 53-65.
Dobler, Barbara, "Direct machine parameter optimization for intensity modulated radiation therapy (IMRT) of propharyngeal cancer—a planning study", Journal of Applied Clinical Medical Physics, vol. 10, No. 4, (Fall 2009), pp. 4-15.
Glassner, A S, "An Introduction to Ray Tracing", Morgan-Kauffman Part 2 out of 2, (1989), 176 pgs.
Gulliford, S, "Generating compensation designs for tangential breast irradiation with artificial neural networks", Physics n Medicine and Biology, vol. 47, (2002), 277-288.
Hardemark, Bjorn, "Direct machine parameter optimization", Philips Medical Systems part Royal Philips Electronics whitepaper, (2004), 8 pgs.
He, Kaiming, "Identity mappings in deep residual networks", European Conference on Computer Vision. Springer, Cham, (2016), 15 pgs.
Neutron Hernandez-Davila, V, "Determination of neutron fluence-to-dose conversion coefficients by means of artificial neural networks", Applied Radiation and Isotopes, vol. 83, (2014), 249-251.
Hesse, Christopher, "Image-to-Image Translation in Tensorflow Make discriminators do your work for you", [Online]. Retrieved from the Internet: URL: https: affinelayer.com pix2pix , (Jan. 25, 2017), 12 pgs.
Hibbard, Lyndon, "Adversarial Prediction of Radiotherapy Treatment Machine Parameters", Advances in Intelligent Data Analysis XIX; [Lecture Notes in Computer Science; Lect.Notes Computer], Springer Internationalpublishing, Cham,, (Oct. 1, 2020), 85-94.

Hua, K L, "Computer-aided classification of lung nodules on computed tomography images via deep learning technique", Onco Targets and Therapy. vol. 8, (2015), 2015-2022.
Bragimov, B., "Development of a Novel Deep Learning Algorithm for Autosegmentation of Clinical Tumor Volume and Organs at Risk in Head and Neck Radiation Therapy Planning", S226 International Journal of Radiation Oncology Biology Physics, (Oct. 1, 2016), p. 1147.
Krizhevsky, Alex, "Imagenet classification with deep convolutional neural networks", Advances in neural Information processings systems, (2012), 1-9.
Kunze-Busch, M., "Efficient SIB-IMRT planning of head and neck patients with Pinnacle—DMPO", MEDICAMUNDI 51 2+3 Nov. 2007, (Nov. 2007), pp. 95-99.
Lecun, Yann, "Deep Learning", Nature vol. 521, (5 28 2015), pp. 436-444.
Mirza, Mehdi, "Conditional generative adversarial nets", arXiv preprint arXiv:1411.1784, (2014), 7 pgs.
Nguyen, Dan, "Dose Prediction with U-net: A Feasibility Study for Predicting Dose Distributions from Contours using Deep Learning on Prostate IMRT Patients", arXiv preprint arXiv:1709.09233, (2017), 17 pgs.
Nie, Dong, "Estimating CT Image from MRI Data Using 3D Fully Convolutional Networks", (Sep. 27, 2016), 9 pgs.
Rafid, Mahmood, "Automated Treatment Planning in Radiation Therapy using Generative Adversarial Networks", Arxiv.Org, Cornell University Library, 201 Olin Library Cornell University Ithaca, NY 14853, XP081113459, (Jul. 17, 2018), 15 pgs.
Shin, H-C, "Interleaved text image deep mining on a very large-scale radiology database.", Proceedings of the IEEE Conference on Computer Vision and Pattern Recognition, (2015), 1090-1099.
Tseng, Huan-Hsin, "Deep reinforcement learning for automated radiation adaptation in lung cancer", Medical physics 44.12, (2017), 6690-6705.
Yu, D, "Automatic Speech Recognition: A Deep Learning Approach", Springer, (2015), 329 pgs.
Parepisheh, Masoud, "A DVH-guided IMRT optimization algorithm for automatic treatment planning and adaptive radiotherapy replanning", Medical physics 41.6Part1, (2014), 061711-1-061711-14.
Zhu, N, "Deep Convolutional Neural Network Image Matching for Ultrasound Guidance in Radiotherapy", [Online], Retrieved from the Internet: URL: http: onlinelibrary.wiley.com doi 10.1118 1.4955603 abstract, (Jun. 2016), 2 pgs.
Zhu, Xiaofeng, "A planning quality evaluation tool for prostate adaptive IMRT based on machine learning", Am. Assoc. Phys. Med. 38 2, (Feb. 2011), pp. 719-726.
Zhu, Xiaofeng, "A planning quality evaluation tool for prostate adaptive IMRT based on machine learning", Medical physics 38.2, (2011), 719-726.
Zuley, M L, "Applying machine learning to radiotherapy planning for head and neck cancer", [Online] Retrieved from the Internet URL:https: deepmind.com blog applying-machine-learning-radiotherapy-planning-head-neck-cancer , (Aug. 30, 2016), 3 pgs.
"International Application Serial No. PCT/US2021/070766, International Search Report dated Mar. 18, 2022", 6 pgs.
"International Application Serial No. PCT/US2021/070766, Written Opinion dated Mar. 18, 2022", 7 pgs.
Goodfellow, Ian, et al., "Deep learning", vol. 1. Cambridge: MIT press, (2016), 802 pgs.
Wang, Wentao, et al., "Fluence Map Prediction Using Deep Learning Models—Direct Plan Generation for Pancreas Stereotactic Body Radiation Therapy", Frontiers in Artificial Intelligence, vol. 3, (Sep. 8, 2020), 68.
"International Application Serial No. PCT US2021 071408, International Preliminary Report on Patentability dated Mar. 30, 2023", 6 pgs.

* cited by examiner

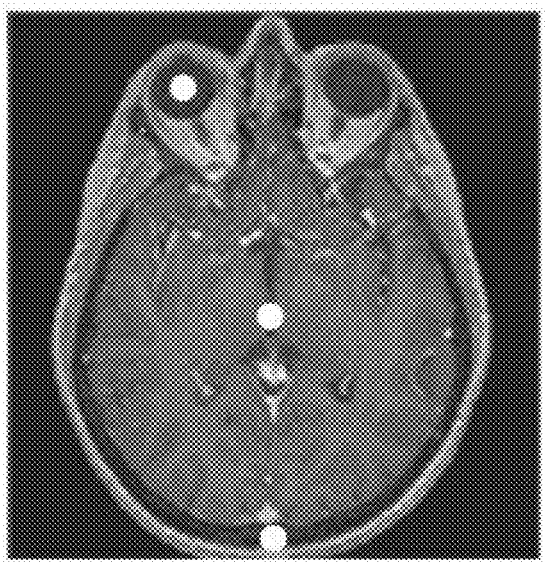 
*FIG. 6A*  *FIG. 6B*

MACHINE LEARNING OPTIMIZATION OF FLUENCE MAPS FOR RADIOTHERAPY TREATMENT

TECHNICAL FIELD

Embodiments of the present disclosure pertain generally to determining plan parameters that direct the radiation therapy performed by a radiation therapy treatment system. In particular, the present disclosure pertains to using machine learning technologies to determine a fluence map used in a treatment plan for a radiation therapy system.

BACKGROUND

Radiation therapy (or "radiotherapy") can be used to treat cancers or other ailments in mammalian (e.g., human and animal) tissue. One such radiotherapy technique is provided using a Gamma Knife, by which a patient is irradiated by a large number of low-intensity gamma rays that converge with high intensity and high precision at a target (e.g., a tumor). Another such radiotherapy technique is provided using a linear accelerator (linac), whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various OARs because as the number of OARs increases (e.g., a dozen or more OARs for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, computed tomography (CT), nuclear magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively or additionally, an automated tool (e.g., ABAS provided by Elekta AB, Sweden) can be used to assist in identifying or delineating the target tumor and organs at risk. A radiation therapy treatment plan ("treatment plan") can then be created using numerical optimization techniques the minimize objective functions composed of clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose.

As part of the treatment planning process for radiotherapy dosing, fluence is determined and evaluated. Fluence is the density of radiation photons or particles normal to the beam direction, whereas dose is related to the energy released in the material when the photons or particles interact with the material atoms. Dose is therefore dependent on the fluence and the physics of the radiation-matter interactions. Significant planning is conducted as part of determining fluence and dosing for a particular patient and treatment plan.

Overview

In some embodiments, methods, systems and computer-readable medium are provided for generating an optimized fluence map or set of fluence maps, used as part of one or more radiotherapy treatment plans. The methods, systems and computer-readable medium may be configured to perform operations comprising: obtaining image data corresponding to a subject of radiotherapy treatment, the image data indicating one or more target dose areas and one or more organs-at-risk areas in the anatomy of the subject; generating anatomy projection images from the image data, each anatomy projection image providing a view of the subject from a respective beam angle of the radiotherapy treatment; and using a trained neural network model to generate estimated fluence maps based on the anatomy projection images, each of the estimated fluence maps indicating a fluence distribution of the radiotherapy treatment at a respective beam angle. In these and other configurations, such a neural network model may be trained with corresponding pairs of anatomy projection images and fluence maps, to produce the estimated fluence map(s).

In some implementations, each of the estimated fluence maps is a two-dimensional array of beamlet weights normal to a respective beam direction, and beam angles of the radiotherapy treatment correspond to gantry angles of a radiotherapy treatment machine. Further, obtaining the three-dimensional set of image data corresponding to a subject may include obtaining and projecting image data for each gantry angle of the radiotherapy treatment machine, such that each generated anatomy projection image represents a view of the anatomy of the subject from a given gantry angle used to provide treatment with a given radiotherapy beam.

In some implementations, the generated estimated fluence maps are used during operations to calculate and optimize radiation doses in the radiotherapy treatment plan, such as for a radiotherapy treatment that provides a volume modulated arc therapy (VMAT) radiotherapy performed by a radiotherapy treatment machine, as multiple radiotherapy beams are shaped to achieve a modulated dose for target areas, from among multiple beam angles, to deliver a prescribed radiation dose. For instance, a workflow for radiotherapy planning may involve: generating a set of estimated fluence maps using the neural network model; performing numerical optimization with the estimated fluence maps as input to the optimization, where the optimization incorporates radiotherapy treatment constraints; and producing a pareto-optimal fluence plan used in the radiotherapy treatment plan for the subject. Such a pareto-optimal fluence plan may be used to generate a set of initial control points corresponding to each of multiple radiotherapy beams, using arc sequencing, and then performing direct aperture optimization, to generate a set of final control points corresponding to each of the multiple radiotherapy beams. Further, the radiotherapy treatment may be performed using the set of final control points, as the set of final control points are used to control multi-leaf collimator (MLC) leaf positions of a radiotherapy treatment machine at a given gantry angle corresponding to a given beam angle.

Other aspects of generating, identifying, and optimizing fluence maps, including with the use of specific neural network training arrangements are disclosed. For example, in a testing or verification setting, a fluence map produced from the neural network model, in response to an input set of anatomy projection images, may be compared with a fluence map produced from another source. Specific model training aspects involving a generative adversarial network (GAN), conditional generative adversarial network (cGAN), and a cycle-consistent generative adversarial network (CycleGAN) are also disclosed.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIGS. 6A and 6B depict the differences between an exemplary MRI image and a corresponding CT image, respectively, according to some examples.

DETAILED DESCRIPTION

Figure 1:
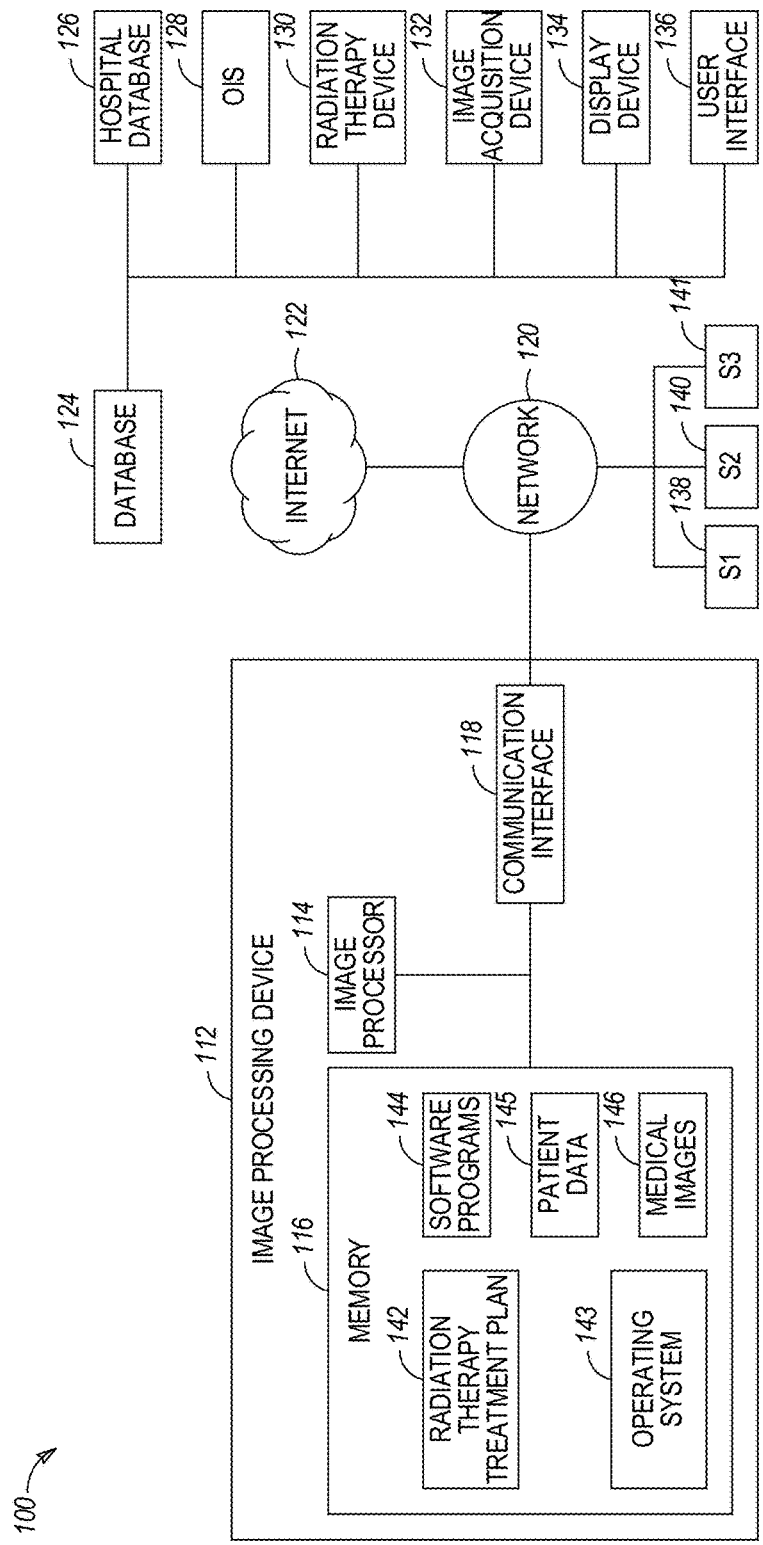
FIG. 1 illustrates an exemplary radiotherapy system, according to some examples.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not to be taken in a limiting sense, and the scope of the present disclosure is defined by the appended claims and their equivalents.

Intensity modulated radiotherapy (IMRT) and volumetric modulated arc therapy (VMAT) have become the standards of care in modern cancer radiation therapy. Creating individual patient IMRT or VMAT treatment plans is often a trial-and-error process, weighing target dose versus OAR sparing tradeoffs, and adjusting program constraints whose effects on the plan quality metrics and the dose distribution can be very difficult to anticipate. Indeed, the order in which the planning constraints are adjusted can itself result in dose differences. Treatment plan quality depends on often subjective judgements by the planner that depend on his/her experience and skill. Even the most skilled planners still have no assurance that their plans are close to the best possible, or whether a little or a lot of effort will result in a significantly better plan.

The present disclosure includes various techniques to improve and enhance radiotherapy treatment by generating fluence map values, as part of a model-driven fluence map optimization (FMO) process during radiotherapy plan design. This model may comprise a trained machine learning model, such as an artificial neural network model, which is trained to produce (predict) a computer-modeled, image-based representation of fluence map values from a given input. These fluence map values may be subsequently used for planning and implementing radiotherapy treatment machine parameters, including the planning and optimization of control points that control radiotherapy machine operations to deliver radiation therapy with treatment to a patient's delineated anatomy.

The technical benefits of these techniques include reduced radiotherapy treatment plan creation time, improved quality in generated radiotherapy treatment plans, and the evaluation of less data or user inputs to produce higher quality fluence map designs. Such technical benefits may result in many apparent medical treatment benefits, including improved accuracy of radiotherapy treatment, reduced exposure to unintended radiation, and the like. The disclosed techniques may be applicable to a variety of medical treatment and diagnostic settings or radiotherapy treatment equipment and devices, including with the use of IMRT and VMAT treatment plans.

FMO is conventionally performed as a numerical computation, producing a 3D dose distribution covering the target while attempting to minimize the effect of dose on nearby OARs. As will be understood, the optimal fluence maps and the resulting 3D dose distribution produced from use of a fluence map are often referred to as a "plan", even though the fluence 3D dose distribution must be resampled and transformed to accommodate linac and multileaf collimator (MLC) properties to become a clinical, deliverable treatment plan. Such changes may include arc segmentation and aperture optimization operations, and other aspects of transformation or modifications, as discussed further below with reference to FIG. 8. However, for purposes of simplicity, references below to a "plan" used below generally refer to the planned radiation dose derived from the fluence map optimization and the outcome of a trained model adapted to produce a fluence map.

Delivering the correct fluence to achieve the desired dose in tissues involves a kind of forward tomography in which 2D arrays of appropriately weighted beamlets are directed through the linac MLC from many angles around the target. The fluence map at each beam angle, in fact, is a 2D array that spans the beam's-eye-view projection image of the target. Each element of the fluence map is a real number weight proportional to the intended dose in the target. VMAT radiotherapy may have 100 or more beams with the total numbers of beamlet weights equal to $10^5$ or more.

Figure 17:
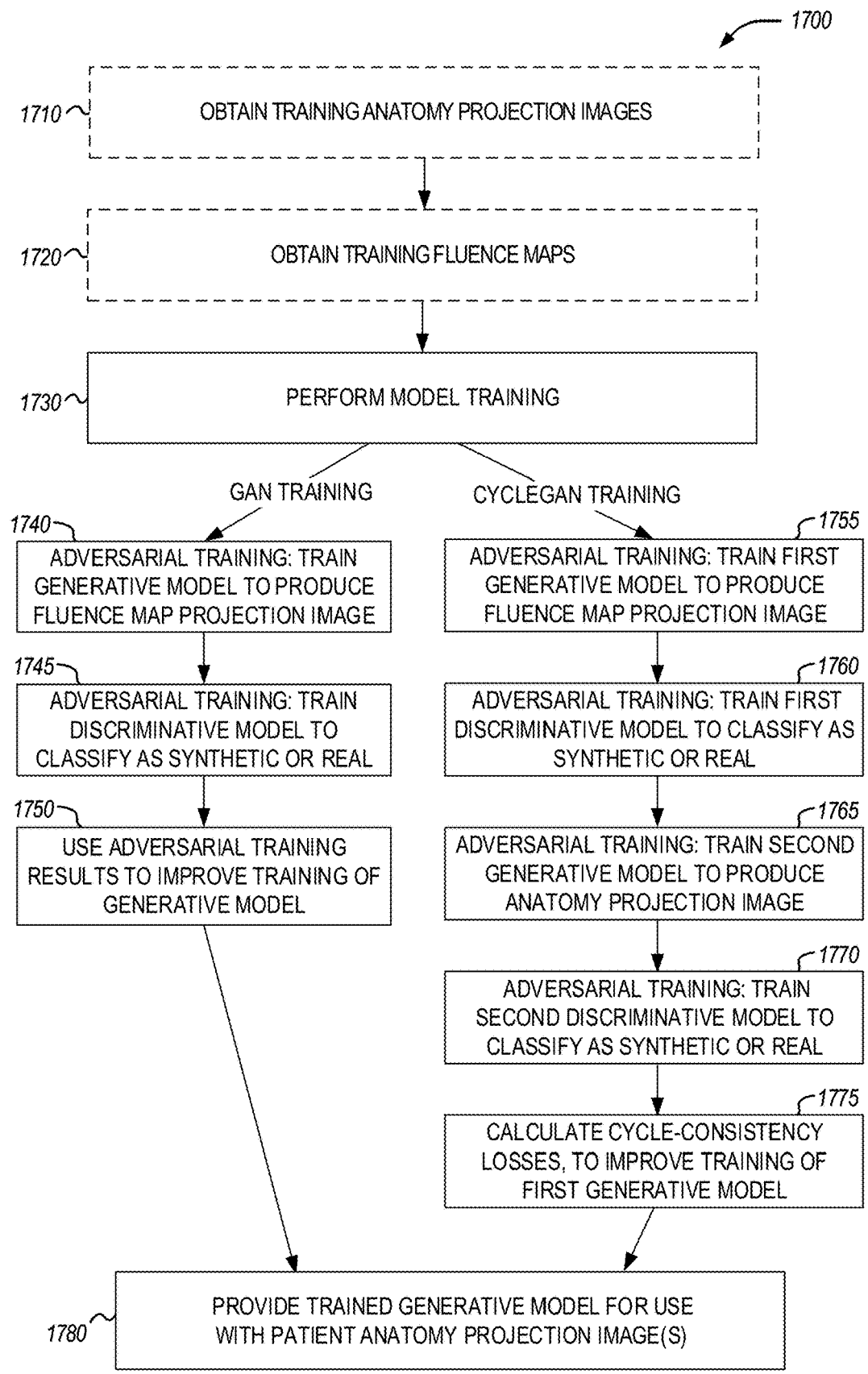
FIGS. 17 and 18 illustrate respective data flows for training and use of a machine learning model adapted to produce simulated fluence maps, according to some examples.
Figure 18:
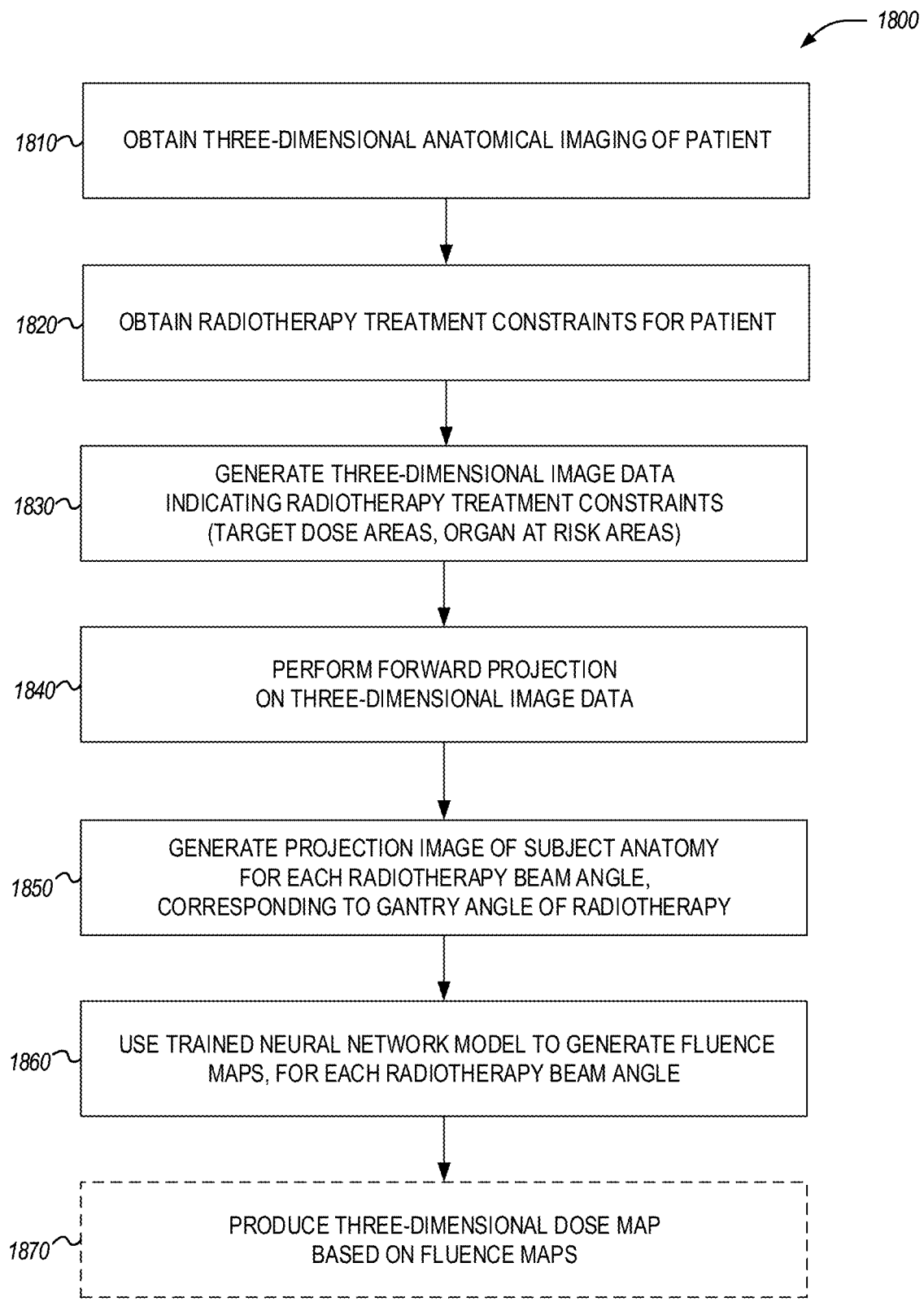
Figure 19:
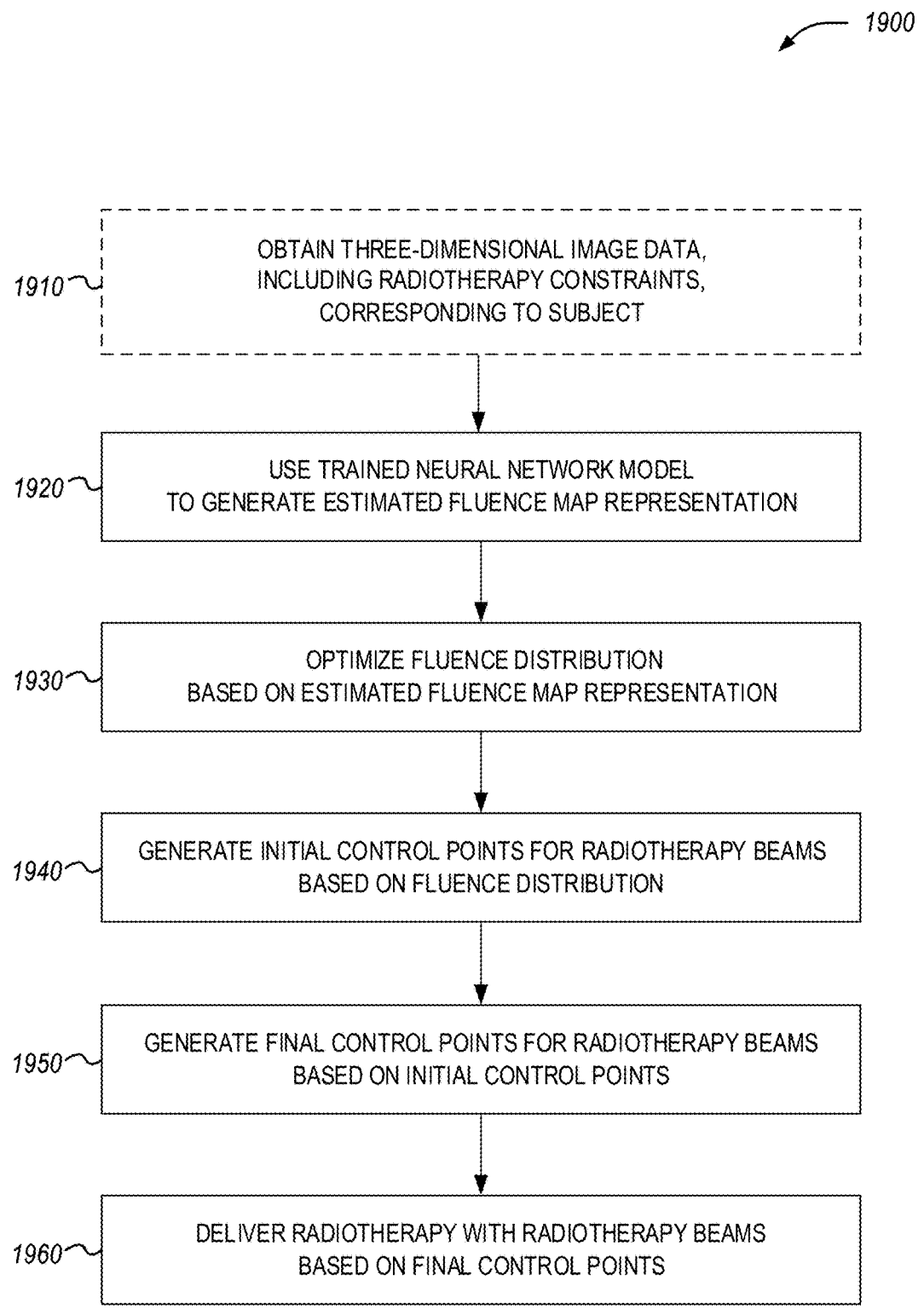
FIG. 19 illustrates a method for generating a fluence map used in a radiotherapy treatment plan and generating the machine parameters to deliver the radiotherapy treatment plan, according to some examples.

FMO performs an exhaustive optimization of target and OAR constraints dependent on thousands of small beamlets aimed at the target from many directions, and the beamlets' weights and physics parameters describing the material fluence dispersion for each beamlet. This high-dimensional optimization typically starts from default initial values for the parameters, without regard to the specific patient's anatomy. Among other techniques, the following discusses creation and training of an anatomy-dependent model of the FMO parameters so the calculation can be initialized closer to the ideal end values for the parameters, thus reducing the time needed to produce a satisfactory fluence map. Additionally, such an anatomy-dependent model of the FMO parameters may be adapted for verification or validation of fluence maps, and integrated in a variety of ways for radiotherapy planning The following paragraphs provide an overview of example radiotherapy system implementations and treatment planning (with reference to FIGS. 2A to 7), including with the use of computing systems and hardware implementations (with reference to FIGS. 1 and 20). The following paragraphs also provide a discussion of considerations specific to fluence map optimization (with reference to FIGS. 8 to 9) and representations of a fluence map relative to patient anatomy projections (with reference to FIGS. 10 to 13). Finally, a discussion of machine learning techniques (with reference to FIGS. 14 to 16B) is provided for methods of training and using a machine learning model (FIGS. 17 to 19).

FIG. 1 illustrates a radiotherapy system 100 for providing radiation therapy to a patient. The radiotherapy system 100 includes an image processing device 112. The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 and plan-related data to be used by the radiation therapy device 130.

The image processing device 112 may include a memory device 116, an image processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., executable implementations of artificial intelligence, deep learning neural networks, radiotherapy treatment plan software), and any other computer-executable instructions to be executed by the processor 114. In an example, the software programs 144 may convert medical images of one format (e.g., MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image); alternatively, the image processing programs may convert a CT image into an MRI image. In another example, the software programs 144 may register the patient image (e.g., a CT image or an MR image) with that patient's dose distribution (also represented as an image) so that corresponding image voxels and dose voxels are associated appropriately by the network. In yet another example, the software programs 144 may substitute functions of the patient images such as signed distance functions or processed versions of the images that emphasize some aspect of the image information. Such functions might emphasize edges or differences in voxel textures, or any other structural aspect useful to neural network learning. In another example, the software programs 144 may substitute functions of a dose distribution that emphasizes some aspect of the dose information. Such functions might emphasize steep gradients around the target or any other structural aspect useful to neural network learning. The memory device 116 may store data, including medical images 146, patient data 145, and other data required to create and implement at least one radiation therapy treatment plan 142 or data associated with at least one plan.

In yet another example, the software programs 144 may generate projection images for a set of two-dimensional (2D) and/or 3D CT or MR images depicting an anatomy (e.g., one or more targets and one or more OARs) representing different views of the anatomy from one or more beam angles used to deliver radiotherapy, which may correspond to respective gantry angles of the radiotherapy equipment. For example, the software programs 144 may process the set of CT or MR images and create a stack of projection images depicting different views of the anatomy depicted in the CT or MR images from various perspectives of the radiotherapy beams, as part of generating fluence data for radiotherapy treatment plan. For instance, one projection image may represent a view of the anatomy from 0 degrees of the gantry, a second projection image may represent a view of the anatomy from 45 degrees of the gantry, and a third projection image may represent a view of the anatomy from 90 degrees of the gantry, with a separate radiotherapy beam being located at each angle. In other examples, each projection image may represent a view of the anatomy from a particular beam angle, corresponding to the position of the radiotherapy beam at the respective angle of the gantry.

Figure 2A:
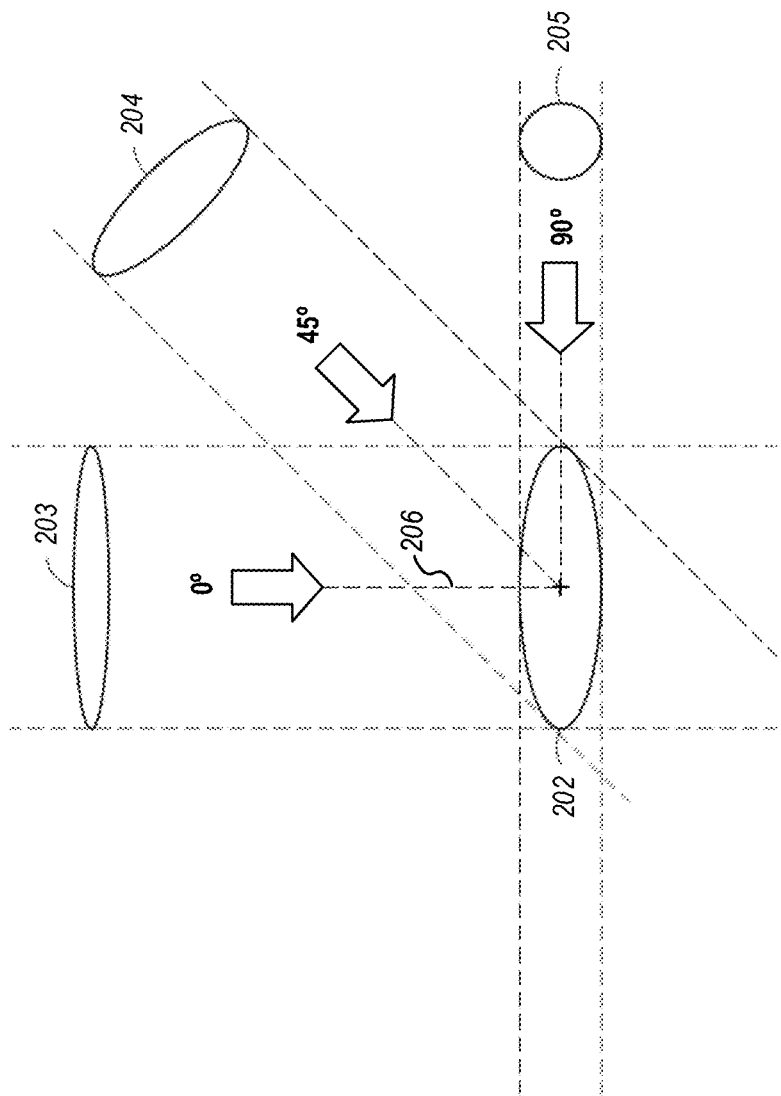
FIGS. 2A and 2B illustrate projection views of an ellipse and an exemplary prostate target anatomy, according to some examples.

Projection views for a simple ellipse 202 are shown schematically in FIG. 2A. In FIG. 2A, the views are oriented relative the ellipse center and capture the shape and extent of the ellipse 202 as seen from each angle (e.g., 0 degrees represented by view 203, 45 degrees represented by view 204, and 90 degrees represented by view 205). For example, the view of ellipse 202 when seen from a 0-degree angle relative to the y-axis 206 of ellipse 202 is projected as view 203. For example, the view of ellipse 202 when seen from a 45-degree angle relative to the y-axis 206 of ellipse 202 is projected as view 204. For example, the view of ellipse 202 when seen from a 90-degree angle relative to the y-axis 206 of ellipse 202 is projected as view 205.

Figure 2B:
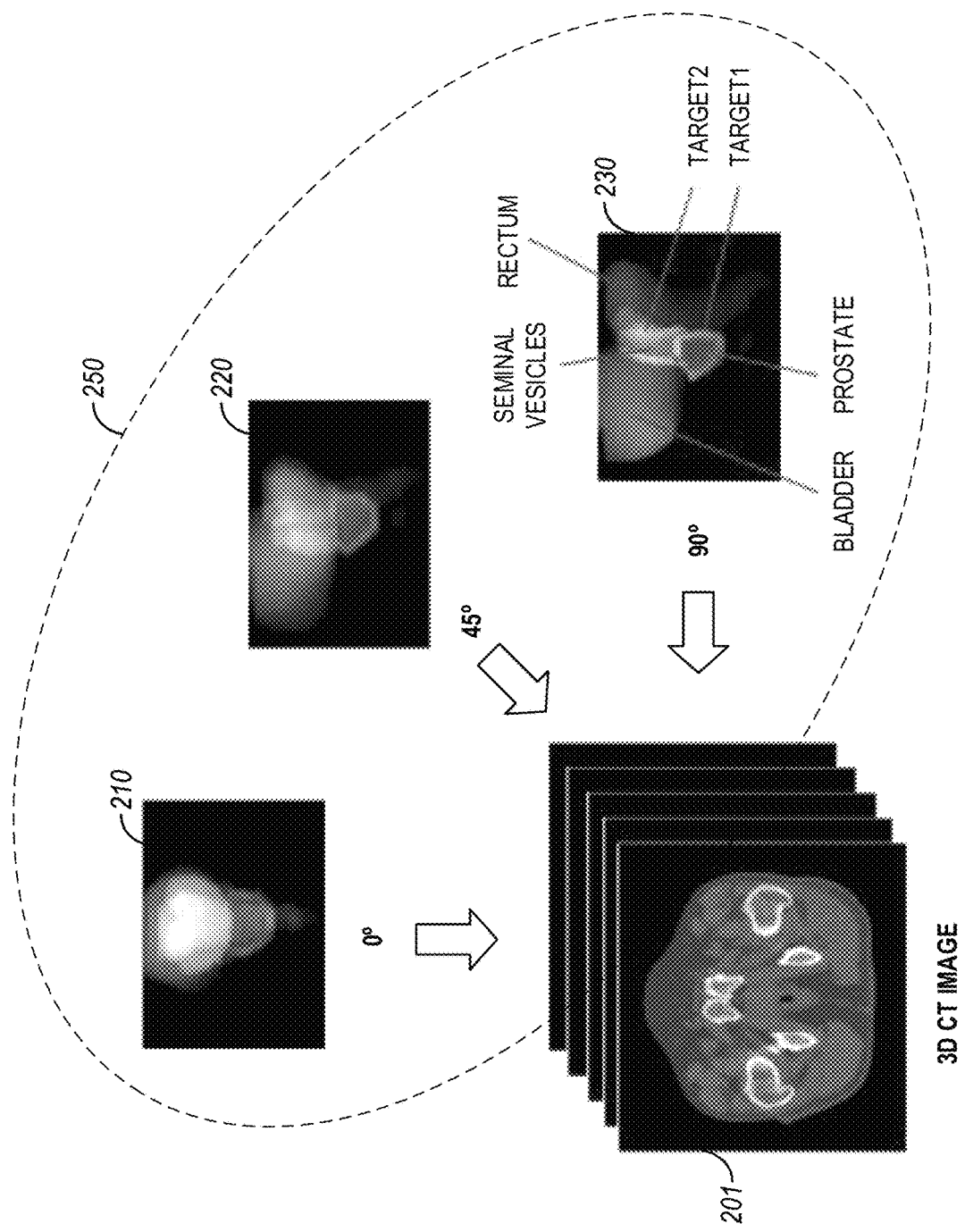

Projections of the male pelvic anatomy relative to a set of original 3D CT images 201 are shown in FIG. 2B. Selected organs at risk and target organs were contoured in the 3D CT image 201 and their voxels were assigned a code value depending on the type of anatomy. Projection images 250 at selected angles (0 degrees, 45 degrees, and 90 degrees) about the central axis of the 3D CT image 201 can be obtained using the forward projection capability of a reconstruction process (e.g., a cone beam CT reconstruction program). Projection images can also be computed either by directly re-creating the projection view geometry by ray tracing or by Fourier reconstruction such as is used in computed tomography.

In an example, the projection image can be computed by tracing the path of light as pixels in an image plane and simulating the effects of its encounters with virtual objects. In some implementations, the projection image is generated by tracing a path from an imaginary eye (a beam's eye view, or an MLC view) through each pixel in a virtual screen and calculating the color of the object visible through it. Other tomographic reconstruction techniques can be utilized to generate the projection images from the views of the anatomy depicted in the 3D CT images 201.

For example, the set of (or collection of) 3D CT images 201 can be used to generate one or more views of the anatomy (e.g., the bladder, prostate, seminal vesicles, rectum, first and second targets) depicted in the 3D CT images 201. The views can be from the perspective of the radiotherapy beam (e.g., as provided by the gantry of the radiotherapy device) and, for simplicity with reference to FIG. 2B, the views are measured in degrees relative to the y-axis of the 3D CT images 201 and based on a distance between the anatomy depicted in the image and the MLC. Specifically, a first view 210 represents a projection of the 3D CT images 201 when viewed or seen from the gantry when the gantry is 0 degrees relative to the y-axis and is at a given distance from the anatomy depicted in the 3D CT image 201, a second view 220 represents a projection of the 3D CT images 201 when viewed or seen by the gantry when the gantry is 45 degrees relative to the y-axis and is at a given distance from the anatomy depicted in the 3D CT image 201, and a third view 230 represents a projection of the 3D CT images 201 when viewed or seen by the gantry when the gantry is 90 degrees relative to the y-axis. Any other views can be provided, such as a different view at each of 360 degrees around the anatomy depicted in the 3D CT images 201.

Referring back to FIG. 1, in yet another example, the software programs 144 may generate graphical image representations of fluence map data (variously referred to as fluence map representations, fluence map images, or "fluence maps") at various radiotherapy beam and gantry angles, using the machine learning techniques discussed herein. In particular, the software programs 144 may optimize information from these fluence map representations in machine learning-assisted aspects of fluence map optimization. Such fluence map data is ultimately used generate and refine a set of control points that control a radiotherapy device to produce a radiotherapy beam. The control points may represent the beam intensity, gantry angle relative to the patient position, and the leaf positions of the MLC, among other machine parameters, to deliver the dose specified by the fluence map representation.

In yet another example, the software programs 144 store a treatment planning software that includes a trained machine learning model, such as a trained generative model from a generative adversarial network (GAN), conditional generative adversarial network (cGAN), or a cycle-consistent generative adversarial network (CycleGAN), to generate or estimate a fluence map image representation at a given radiotherapy beam angle, based on input to the model of a projection image of the anatomy representing the view of the anatomy from the given angle, and the treatment constraints (e.g., target doses and organs at risk) in such anatomy. The software programs 144 may further store a function to optimize or accept further optimization of the fluence map data, and to convert or compute the fluence maps into machine parameters or control points for a given type of radiotherapy machine (e.g., to output a beam from a MLC to achieve a fluence map using the MLC leaf positions). As a result, the treatment planning software may perform a number of computations to adapt the beam shape and intensity for each radiotherapy beam and gantry angle to the radiotherapy treatment constraints, and to compute the control points for a given radiotherapy device to achieve that beam shape and intensity in the subject patient.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer-executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 to be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information; or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a machine learning model, such as a neural network model; or generate intermediate 2D or 3D images, which may then subsequently be stored in memory device 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software programs 144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application-specific integrated circuit (ASIC), a field programmable gate array (FPGA), a digital signal processor (DSP), a System on a Chip (SoC), or the like. As would be appreciated by those skilled in the art, in some examples, the processor 114 may be a special-purpose processor, rather than a general-purpose processor. The processor 114 may include one or more known processing devices, such as a microprocessor from the Pentium™, Core™, Xeon™ or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed examples are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory device 116, to perform various operations, processes, methods that will be explained in greater detail below.

The memory device 116 can store medical images 146. In some examples, the medical images 146 may include one or more MRI images (e.g., 2D MRI, 3D MRI, 2D streaming MRI, four-dimensional (4D) MRI, 4D volumetric Mill, 4D cine MRI, projection images, fluence map representation images, graphical aperture images, pairing information between projection images and fluence map representation images, and pairing information between projection images and graphical aperture images, etc.), functional MRI images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, contoured images, and dose images. In an example, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and URI imaging device, or other medical imaging devices for obtaining the medical images of the patient. The medical images 146 may be received and stored in any type of data or any type of format that the image processing device 112 may use to perform operations consistent with the disclosed examples.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory device 116. The communication interface 118 may provide communication connections between the image processing device 112 and radiotherapy system 100 components (e.g., permitting the exchange of data with external devices). For instance, the communication interface 118 may in some examples have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a Wi-Fi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some examples, one or more of the systems in network 120 may form a distributed computing/simulation environment that collaboratively performs the examples described herein. In some examples, one or more systems S1, S2, and S3 may include a CT scanner that obtains CT images (e.g., medical images 146). In addition, network 120 may be connected to Internet 122 to communicate with servers and clients that reside remotely on the Internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some examples, database 124 may include a processor-readable storage medium (not shown). While the processor-readable storage medium in an example may be a single medium, the term "processor-readable storage medium" should be taken to include a single medium or multiple media (e.g., a centralized or distributed database, and/or associated caches and servers) that store the one or more sets of computer-executable instructions or data. The term "processor-readable storage medium" shall also be taken to include any medium that is capable of storing or encoding a set of instructions for execution by a processor and that cause the processor to perform any one or more of the methodologies of the present disclosure. The term "processor-readable storage medium" shall accordingly be taken to include, but not be limited to, solid-state memories, optical and magnetic media. For example, the processor-readable storage medium can be one or more volatile, non-transitory, or non-volatile tangible computer-readable media.

Image processor 114 may communicate with database 124 to read images into memory device 116 or store images from memory device 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) data, projection images, graphical aperture images, etc.) that the database 124 received from image acquisition device 132. Database 124 may store data to be used by the image processor 114 when executing software program 144, or when creating radiation therapy treatment plans 142. Database 124 may store the data produced by the trained machine leaning mode, such as a neural network including the network parameters constituting the model learned by the network and the resulting predicted data. The image processing device 112 may receive the imaging data, such as a medical image 146 (e.g., 2D MRI slice images, CT images, 2D Fluoroscopy images, X-ray images, 3DMRI images, 4D MRI images, projection images, graphical aperture images, etc.) either from the database 124, the radiation therapy device 130 (e.g., an MRI-linac), and/or the image acquisition device 132 to generate a radiation therapy treatment plan 142.

In an example, the radiotherapy system 100 can include an image acquisition device 132 that can acquire medical images (e.g., MRI images, 3D MRI, 2D streaming MRI, 4D volumetric MRI, CT images, cone-Beam CT, PET images, functional MRI images (e.g., Mill, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can also be stored by the image processing device 112, as medical images 146 in memory device 116.

In an example, the image acquisition device 132 may be integrated with the radiation therapy device 130 as a single apparatus (e.g., an MRI-linac). Such an MRI-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In an example, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The image processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the image processor 114 may communicate with the image acquisition device 132 (e.g., a CT device, an MRI device, a PET device, an X-ray device, an ultrasound device, etc.) to access images of the patient and to delineate a target, such as a tumor. In some examples, the delineation of one or more OARs, such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as Mill images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images 146, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be Obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, and a successor auto-segmentation software product ADMIRE™, manufactured by Elekta AB of Stockholm, Sweden). In certain examples, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device with which a user may input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, the image acquisition device 132 could be implemented as a virtual machine. Given the processing power, memory, and computational capability available, the entire radiotherapy system 100 could be implemented as a virtual machine.

Figure 3A:
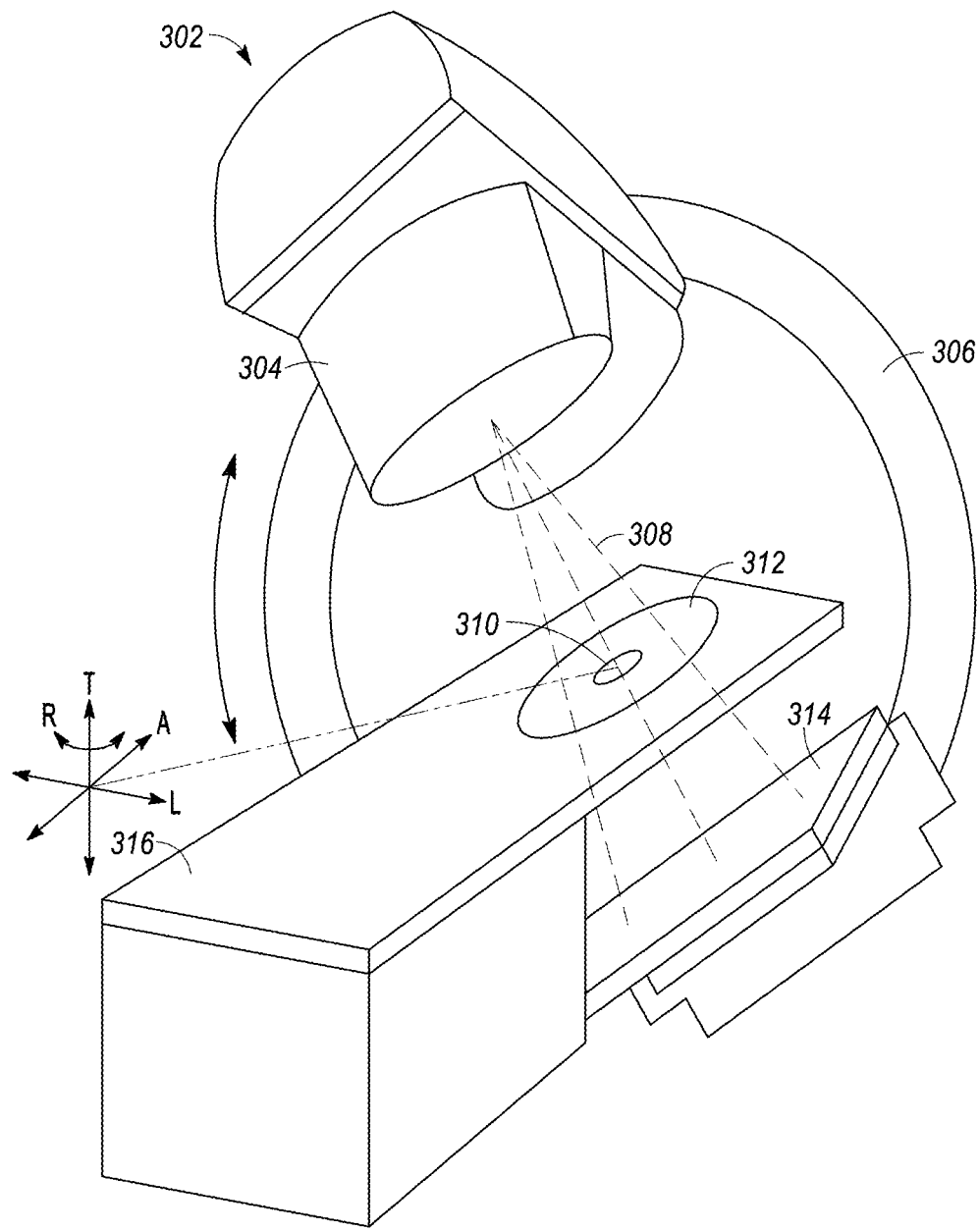
FIG. 3A illustrates an exemplary radiation therapy system that can include radiation therapy output configured to provide a therapy beam, according to some examples.

FIG. 3A illustrates a radiation therapy device 302 that may include a radiation source, such as an X-ray source or a linear accelerator, a couch 316, an imaging detector 314, and a radiation therapy output 304. The radiation therapy device 302 may be configured to emit a radiation beam 308 to provide therapy to a patient. The radiation therapy output 304 can include one or more attenuators or collimators, such as an MLC as described in the illustrative example of FIG. 7, below.

Referring back to FIG. 3A, a patient can be positioned in a region 312 and supported by the treatment couch 316 to receive a radiation therapy dose, according to a radiation therapy treatment plan. The radiation therapy output 304 can be mounted or attached to a gantry 306 or other mechanical support. One or more chassis motors (not shown) may rotate the gantry 306 and the radiation therapy output 304 around couch 316 when the couch 316 is inserted into the treatment area. In an example, gantry 306 may be continuously rotatable around couch 316 when the couch 316 is inserted into the treatment area. In another example, gantry 306 may rotate to a predetermined position when the couch 316 is inserted into the treatment area. For example, the gantry 306 can be configured to rotate the therapy output 304 around an axis ("A"). Both the couch 316 and the radiation therapy output 304 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 316 movements or rotations in order to properly position the patient in or out of the radiation beam 308 according to a radiation therapy treatment plan. Both the couch 316 and the gantry 306 are independently moveable from one another in multiple degrees of freedom, which allows the patient to be positioned such that the radiation beam 308 can target the tumor precisely. The MLC may be integrated and included within gantry 306 to deliver the radiation beam 308 of a certain shape.

The coordinate system (including axes A, T, and L) shown in FIG. 3A can have an origin located at an isocenter 310. The isocenter can be defined as a location where the central axis of the radiation beam 308 intersects the origin of a coordinate axis, such as to deliver a prescribed radiation dose to a location on or within a patient. Alternatively, the isocenter 310 can be defined as a location where the central axis of the radiation beam 308 intersects the patient for various rotational positions of the radiation therapy output 304 as positioned by the gantry 306 around the axis A. As discussed herein, the gantry angle corresponds to the position of gantry 306 relative to axis A, although any other axis or combination of axes can be referenced and used to determine the gantry angle.

Gantry 306 may also have an attached imaging detector 314. The imaging detector 314 is preferably located opposite to the radiation source, and in an example, the imaging detector 314 can be located within a field of the radiation beam 308.

The imaging detector 314 can be mounted on the gantry 306 (preferably opposite the radiation therapy output 304), such as to maintain alignment with the therapy beam 308. The imaging detector 314 rotates about the rotational axis as the gantry 306 rotates. In an example, the imaging detector 314 can be a flat panel detector (e.g., a direct detector or a scintillator detector). In this manner, the imaging detector 314 can be used to monitor the radiation beam 308 or the imaging detector 314 can be used for imaging the patient's anatomy, such as portal imaging. The control circuitry of the radiation therapy device 302 may be integrated within the radiotherapy system 100 or remote from it.

In an illustrative example, one or more of the couch 316, the therapy output 304, or the gantry 306 can be automatically positioned, and the therapy output 304 can establish the radiation beam 308 according to a specified dose for a particular therapy delivery instance. A sequence of therapy deliveries can be specified according to a radiation therapy treatment plan, such as using one or more different orientations or locations of the gantry 306, couch 316, or therapy output 304. The therapy deliveries can occur sequentially, but can intersect in a desired therapy locus on or within the patient, such as at the isocenter 310. A prescribed cumulative dose of radiation therapy can thereby be delivered to the therapy locus while damage to tissue near the therapy locus can be reduced or avoided.

Figure 3B:
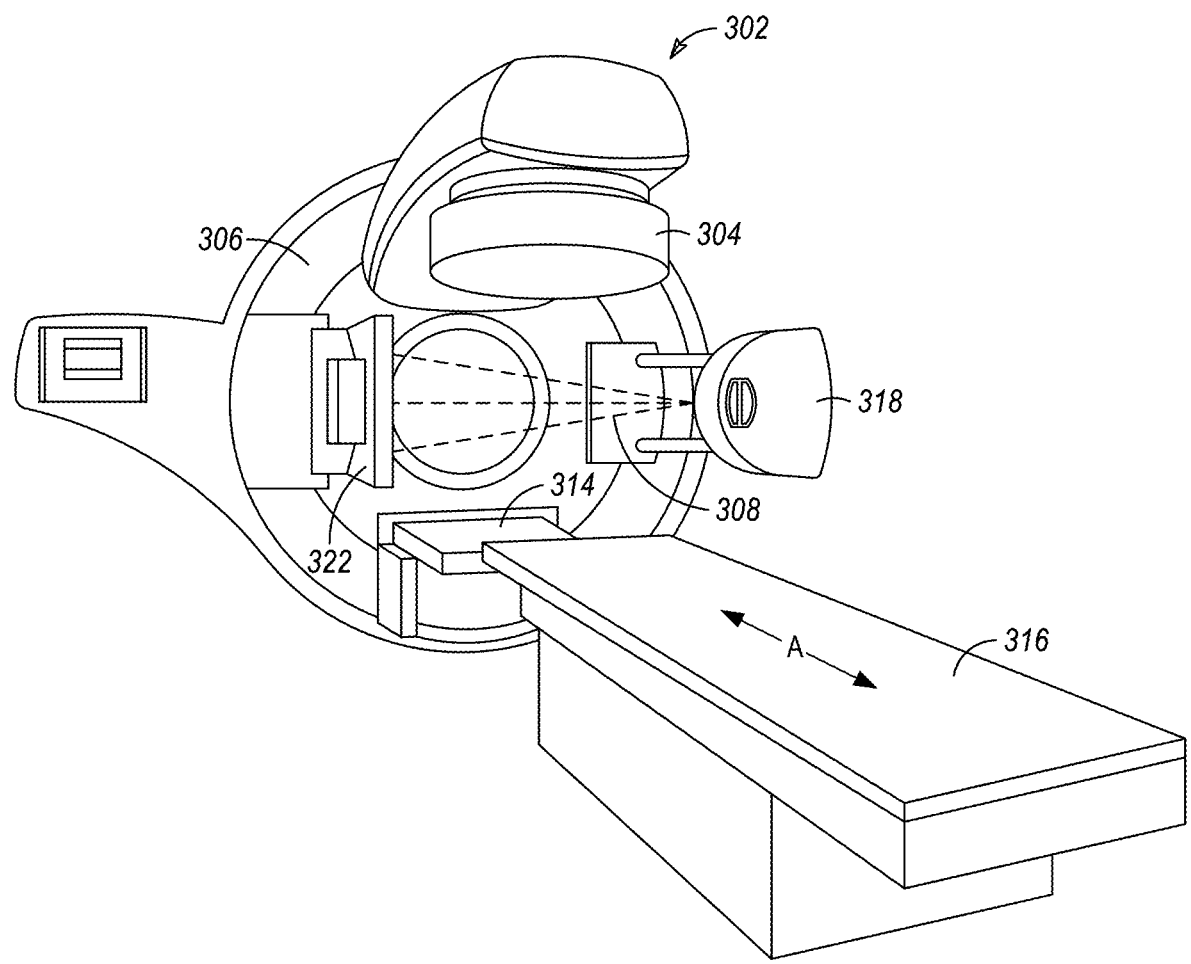
FIG. 3B illustrates an exemplary system including a combined radiation therapy system and an imaging system, such as a cone beam computed tomography (CBCT) imaging system, according to some examples.

FIG. 3B illustrates a radiation therapy device 302 that may include a combined linac and an imaging system, such as a CT imaging system. The radiation therapy device 302 can include an MLC (not shown). The CT imaging system can include an imaging X-ray source 318, such as providing X-ray energy in a kiloelectron-Volt (keV) energy range. The imaging X-ray source 318 can provide a fan-shaped and/or a conical radiation beam 308 directed to an imaging detector 322, such as a flat panel detector. The radiation therapy device 302 can be similar to the system described in relation to FIG. 3A, such as including a radiation therapy output 304, a gantry 306, a couch 316, and another imaging detector 314

(such as a flat panel detector). The X-ray source 318 can provide a comparatively-lower-energy X-ray diagnostic beam, for imaging.

In the illustrative example of FIG. 3B, the radiation therapy output 304 and the X-ray source 318 can be mounted on the same rotating gantry 306, rotationally separated from each other by 90 degrees. In another example, two or more X-ray sources can be mounted along the circumference of the gantry 306, such as each having its own detector arrangement to provide multiple angles of diagnostic imaging concurrently. Similarly, multiple radiation therapy outputs 304 can be provided.

Figure 4:
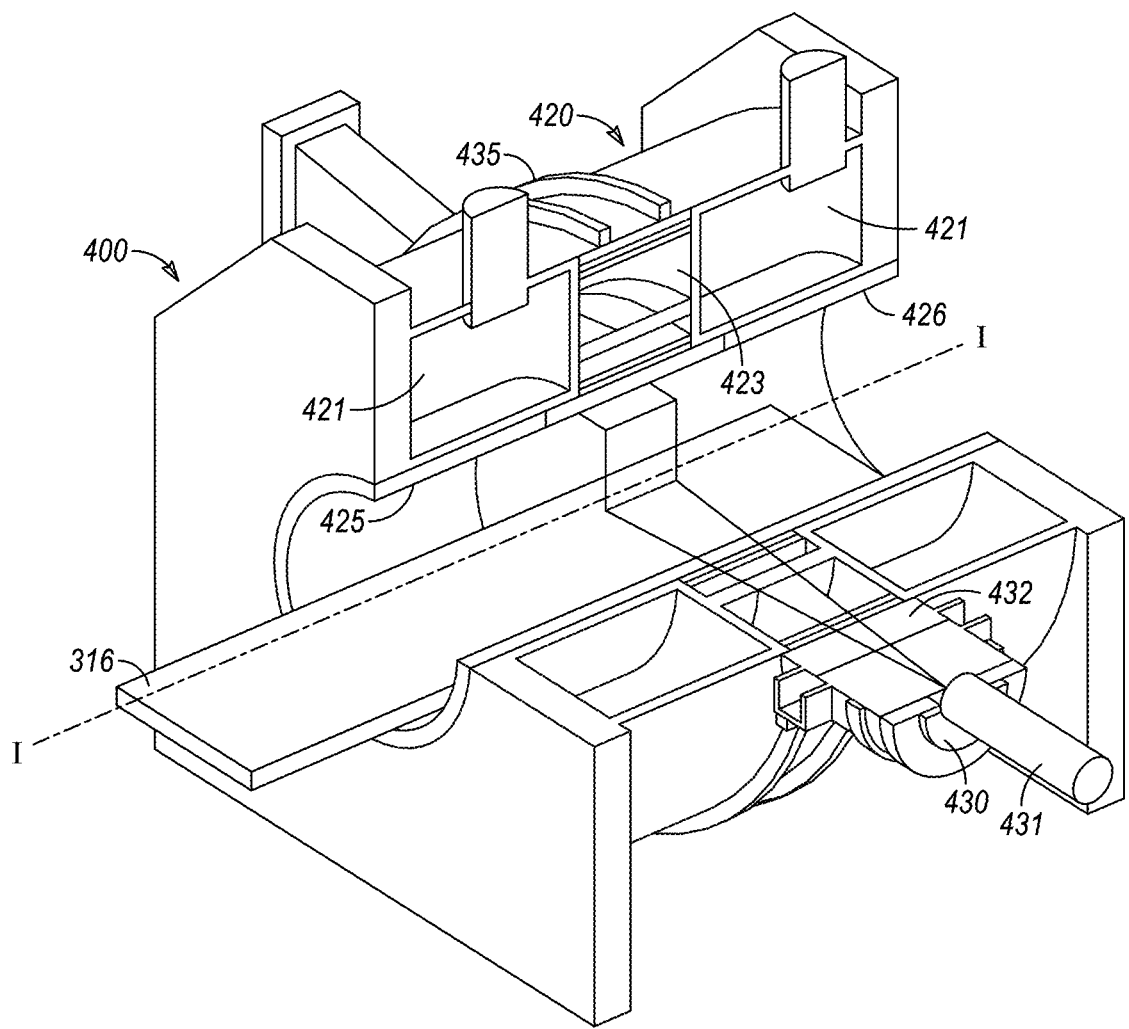
FIG. 4 illustrates a partially cut-away view of an exemplary system including a combined radiation therapy system and an imaging system, such as a nuclear magnetic resonance (MR) imaging (MM) system, according to some examples.

FIG. 4 depicts a radiation therapy system 400 that can include combining a radiation therapy device (e.g., radiation therapy device 302 from FIG. 31 and an imaging system, such as a magnetic resonance (MR) imaging system (e.g., known in the art as an MR-linac) consistent with the disclosed examples. As shown, system 400 may include a couch 316, an image acquisition device 420, and a radiation delivery device 430. System 400 delivers radiation therapy to a patient in accordance with a radiotherapy treatment plan. In some examples, image acquisition device 420 may correspond to image acquisition device 132 in FIG. 1 that may acquire origin images of a first modality (e.g., MRI image shown in FIG. 6A) or destination images of a second modality (e.g., CT image shown in FIG. 611).

Couch 316 may support a patient (not shown) during a treatment session. In some implementations, couch 316 may move along a horizontal translation axis (labelled "I"), such that couch 316 can move the patient resting on couch 316 into and/or out of system 400. Couch 316 may also rotate around a central vertical axis of rotation, transverse to the translation axis. To allow such movement or rotation, couch 316 may have motors (not shown) enabling the couch 316 to move in various directions and to rotate along various axes. A controller (not shown) may control these movements or rotations in order to properly position the patient according to a treatment plan.

In some examples, image acquisition device 420 may include an MRI machine used to acquire 2D or 3D MRI images of the patient before, during, and/or after a treatment session. Image acquisition device 420 may include a magnet 421 for generating a primary magnetic field for magnetic resonance imaging. The magnetic field lines generated by operation of magnet 421 may run substantially parallel to the central translation axis I. Magnet 421 may include one or more coils with an axis that runs parallel to the translation axis I. In some examples, the one or more coils in magnet 421 may be spaced such that a central window 423 of magnet 421 is free of coils. In other examples, the coils in magnet 421 may be thin enough or of a reduced density such that they are substantially transparent to radiation of the wavelength generated by radiation delivery device 430, Image acquisition device 420 may also include one or more shielding coils, which may generate a magnetic field outside magnet 421 of approximately equal magnitude and opposite polarity in order to cancel or reduce any magnetic field outside of magnet 421. As described below, radiation source 431 of radiation delivery device 430 may be positioned in the region where the magnetic field is cancelled, at least to a first order, or reduced.

Image acquisition device 420 may also include two gradient coils 425 and 426, which may generate a gradient magnetic field that is superposed on the primary magnetic field. Coils 425 and 426 may generate a gradient in the resultant magnetic field that allows spatial encoding of the protons so that their position can be determined. Gradient coils 425 and 426 may be positioned around a common central axis with the magnet 421 and may be displaced along that central axis. The displacement may create a gap, or window, between coils 425 and 426. In examples where magnet 421 can also include a central window 423 between coils, the two windows may be aligned with each other.

In some examples, image acquisition device 420 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 420 concerns certain examples and is not intended to be limiting.

Figure 7:
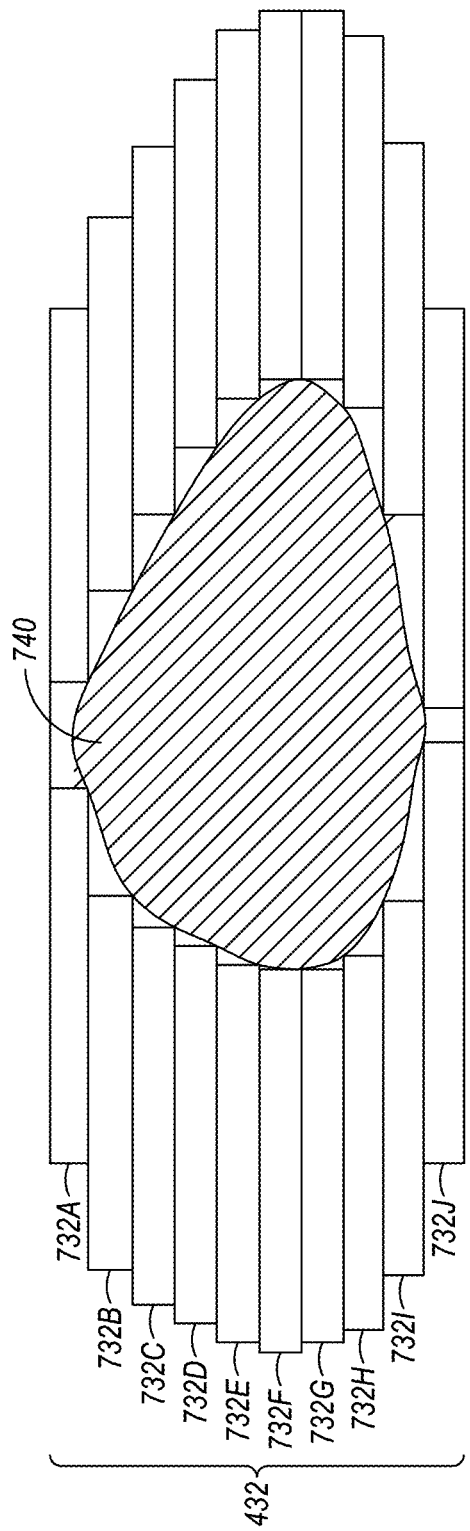
FIG. 7 illustrates an exemplary collimator configuration for shaping, directing, or modulating an intensity of a radiation therapy beam, according to some examples.

Radiation delivery device 430 may include the radiation source 431, such as an X-ray source or a linac, and an WC 432 (shown below in more detail in FIG. 7). Radiation delivery device 430 may be mounted on a chassis 435. One or more chassis motors (not shown) may rotate the chassis 435 around the couch 316 when the couch 316 is inserted into the treatment area. In an example, the chassis 435 may be continuously rotatable around the couch 316, when the couch 316 is inserted into the treatment area. Chassis 435 may also have an attached radiation detector (not shown), preferably located opposite to radiation source 431 and with the rotational axis of the chassis 435 positioned between the radiation source 431 and the detector. Further, the radiation delivery device 430 may include control circuitry (not shown) used to control, for example, one or more of the couch 316, image acquisition device 420, and radiation delivery device 430. The control circuitry of the radiation delivery device 430 may be integrated within the system 400 or remote from it.

During a radiotherapy treatment session, a patient may be positioned on couch 316. System 400 may then move couch 316 into the treatment area defined by the magnet 421, coils 425, 426, and chassis 435. Control circuitry may then control radiation source 431, MLC 432, and the chassis motor(s) to deliver radiation to the patient through the window between coils 425 and 426 according to a radiotherapy treatment plan.

FIG. 3A, FIG. 3B, and FIG. 4 illustrate generally examples of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

Figure 5:
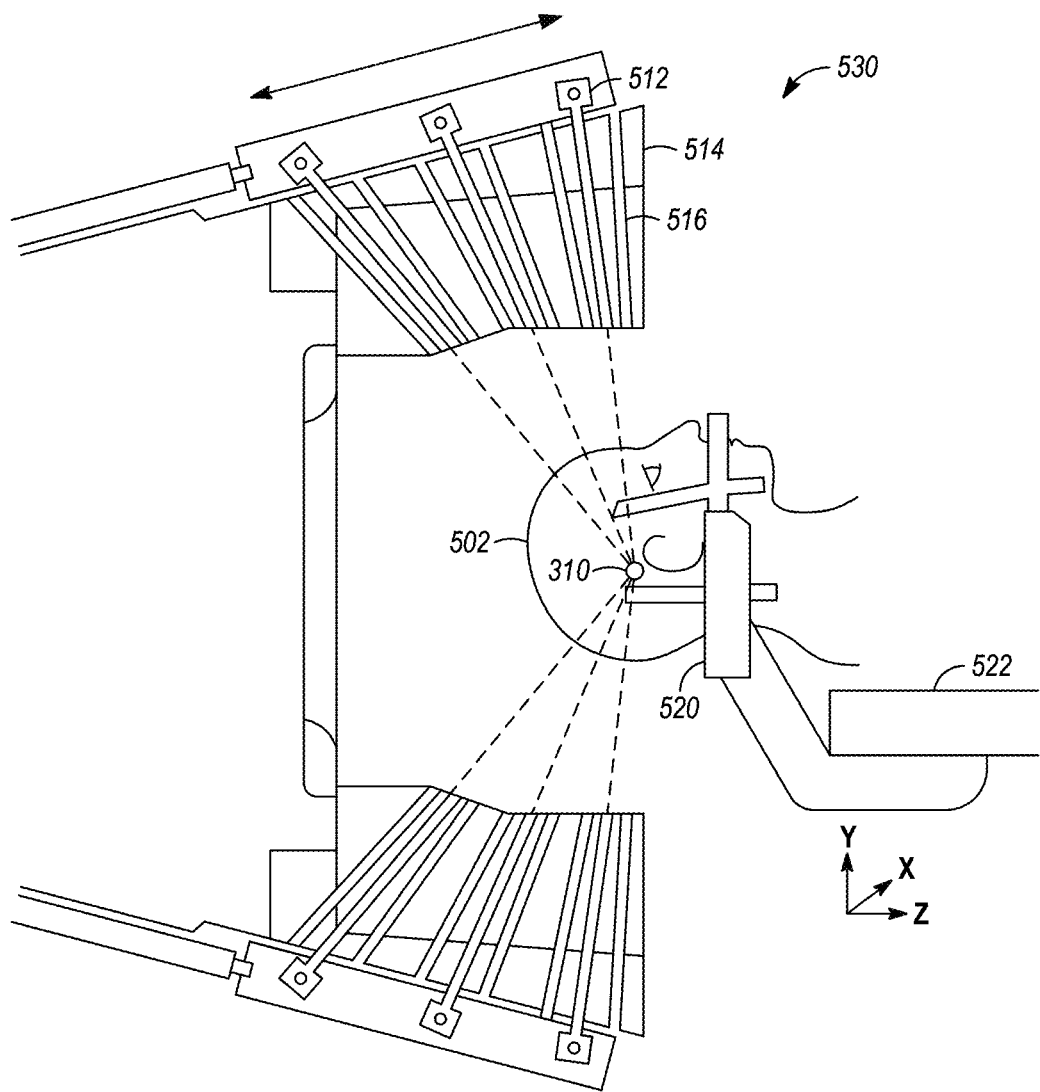
FIG. 5 illustrates an exemplary Gamma Knife radiation therapy system, according to some examples.

FIG. 5 illustrates an example of another type of radiotherapy device 530 (e.g., a Leksell Gamma Knife). As shown in FIG. 5, in a radiotherapy treatment session, a patient 502 may wear a coordinate frame 520 to keep stable the patient's body part (e.g., the head) undergoing surgery or radiotherapy. Coordinate frame 520 and a patient positioning system 522 may establish a spatial coordinate system, which may be used while imaging a patient or during radiation surgery. Radiotherapy device 530 may include a protective housing 514 to enclose a plurality of radiation sources 512. Radiation sources 512 may generate a plurality of radiation beams (e.g., beamlets) through beam channels 516. The plurality of radiation beams may be configured to focus on an isocenter 310 from different directions. While each individual radiation beam may have a relatively low intensity, isocenter 310 may receive a relatively high level of radiation when multiple doses from different radiation beams accumulate at isocenter 310. In certain examples, isocenter 310 may correspond to a target under surgery or treatment, such as a tumor.

As discussed above, radiation therapy devices described by FIG. 3A, FIG. 3B, and FIG. 4 include an MLC for shaping, directing, or modulating an intensity of a radiation therapy beam to the specified target locus within the patient. FIG. 7 illustrates an MLC 432 that includes leaves 732A through 732J that can be automatically positioned to define an aperture approximating a tumor 740 cross-section or projection. The leaves 732A through 732J permit modulation of the radiation therapy beam. The leaves 732A through 732J can be made of a material specified to attenuate or block the radiation beam in regions other than the aperture, in accordance with the radiation treatment plan. For example, the leaves 732A through 732J can include metallic plates, such as comprising tungsten, with a long axis of the plates oriented parallel to a beam direction and having ends oriented orthogonally to the beam direction (as shown in the plane of the illustration of FIG. 2A). A "state" of the MLC 432 can be adjusted adaptively during a course of radiation therapy treatment, such as to establish a therapy beam that better approximates a shape or location of the tumor 740 or other target locus. This is in comparison to using a static collimator configuration or as compared to using an MLC configuration determined exclusively using an "offline" therapy planning technique. A radiation therapy technique using the MLC 432 to produce a specified radiation dose distribution to a tumor or to specific areas within a tumor can be referred to as IMRT. The resulting beam shape that is output using the MLC 432 is represented as a graphical aperture image. Namely, a given graphical aperture image is generated to represent how a beam looks (beam shape) and its intensity after being passed through and output by MLC 432.

IMRT techniques involve irradiating a subject patient at a small number of fixed gantry angles; whereas VMAT techniques typically involve irradiating a subject patient from 100 or more gantry angles. Specifically, with VMAT radiotherapy devices, the patient is irradiated continuously by a linac revolving around the patient with a beam continuously shaped by MLC producing apertures to achieve a modulated coverage of the target, from each angle, by a prescribed radiation dose. VMAT has become popular because it accurately irradiates targets while minimizing dose to neighboring OARs, and VMAT treatments generally take less time than those of IMRT.

Creating plans personalized for every patient using either IMRT or VMAT is difficult. Treatment planning systems model the physics of radiation dose, but they provide little assistance to the planner to indicate how to vary treatment parameters to achieve high quality plans. Changing plan variables often produces nonintuitive results, and the treatment planning system is unable to tell the planner whether a little or a lot of effort will be needed to advance the current plan-in-progress to a clinically usable plan. Automated multicriteria optimization reduces planning uncertainty by automated, exhaustive numerical optimizations satisfying a hierarchy of target-OAR constraints, but this method is time consuming and often does not produce a deliverable plan.

Figure 8:
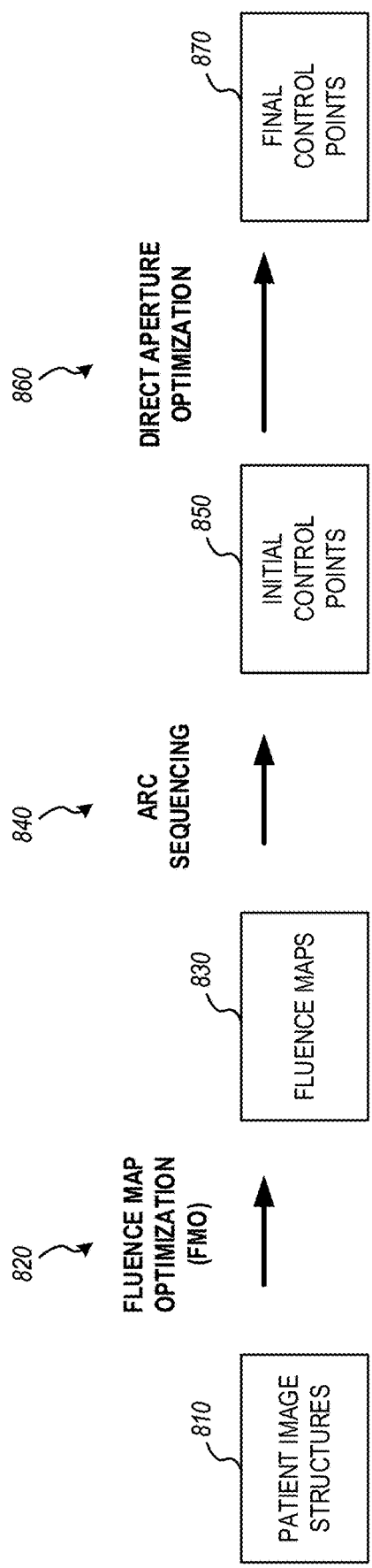
FIG. 8 illustrates a data flow and processes for radiotherapy plan development, according to some examples.

Radiotherapy plan creation typically involves the application of multiple processes to address treatment plan considerations. FIG. 8 illustrates a data flow through the three typical stages of VMAT plan development: Fluence map optimization (FMO) 820, Arc sequencing 840, and Direct aperture optimization 860. As shown in FIG. 8, patient image structures 810, such as image data received from CT, MRI, or similar imaging modalities, are received as input for treatment planning. Through a process of fluence map optimization 820, a fluence map 830 is identified and created. For VMAT plans, the fluence map 830 represents the ideal target dose coverage that must be replicated by constructing segments (MLC apertures and monitor unit weights) at a set of linac gantry angles.

Specifically, the fluence map 830 provides a model of an ideal 3D dose distribution for a radiotherapy treatment, and is constructed during fluence map optimization (FMO) 820. FMO is a hierarchical, multicriteria, numerical optimization that models the irradiation of the target with many small X-ray beamlets subject to target dose and OAR constraints. The resulting fluence maps 830 represent 2D arrays of beamlets' weights that map the radiation onto a beam's-eye-view of the target; thus, in planning a VMAT treatment, there is a fluence map for each VMAT beam at every one of the 100 or more angle settings of the linac gantry encircling the patient. Since fluence is the density of rays traversing a unit surface normal to the beam direction, and dose is the energy released in the irradiated material, the resulting 3D dose covering the target is specified by the set of 2D fluence maps.

The 3D dose that is represented in a fluence map 830, produced from FMO 820, does not include sufficient information about how a machine can deliver radiation to achieve that distribution. Therefore, an initial set of linac/MLC weighted apertures (one set per gantry angle; also called a control point) must be created by iterative modelling of the 3D dose by a succession of MLC apertures at varying gantry angles and with appropriate intensities or weights. These initial control points 850 are produced from arc sequencing 840, with the resulting apertures and parameters of (initial control points 850) being dependent on the specific patient's anatomy and target geometries.

Even with the generation of many control points 850, additional refinement of the apertures and weights is often involved, occasionally adding or subtracting a control point. Refinement is necessary since the 3D dose distribution resulting from arc sequencing 840 is degraded with respect to the original optimal fluence map 830, and some refinement of the apertures invariably improves the resulting plan quality. The process of optimizing the apertures of these control points is referred to as direct aperture optimization 860, with the resulting refined apertures and weights (final control points 870) being dependent on the specific patient's anatomy and target geometries.

In each of the operations 820, 840, 860, an achievable solution corresponds to the minimum value of an objective function in a high-dimensional space that may have many minima and requires lengthy numerical optimizations. In each case, the objective function describes a mapping or relationship between the patient's anatomic structures and a dose distribution or set of linac/MLC machine parameters. The following techniques discuss a mechanism by which the generation of fluence maps 830 and the process of fluence map optimization 820 can itself be optimized from modeling. Specifically, the optimization of a fluence map may occur through the generation of a fluence map using a probabilistic model, such as with a learned model that is trained via machine learning techniques.

Probabilistic modeling of a fluence maps, based on a model that is learned from populations of clinical plans, can provide two significant benefits to the FMO operations discussed in FIG. 8. One benefit from use of a probabilistic model is to accelerate the search for a solution. Using a trained probabilistic model, a new patient's structures can be used to infer fluence maps (e.g., fluence maps 830) that approximates a true solution. This approximation of the solution can serve as a starting point for the numerical optimization and lead to a correct solution (e.g., the final control points 870) in less time than starting from a point with less information. Another benefit from use of a probabilistic model involves the use of approximations to reliably achieve higher quality results than would be obtained by starting with less information. For instance, in some settings, the inferred fluence maps can serve as a lower bound on the expected quality of optimization of a fluence map.

FMO is a high-dimensional optimization that conventionally uses default initial values of the problem parameters, without regard to the specific patient's anatomy. FMO is also performed to produce pareto-optimal results, meaning that the resulting dose distribution satisfies the target and OAR constraints such that no constraint can be improved without degrading another. Achieving this high level of accuracy requires exhaustive computations adjusting beamlet weights in the beam-normal fluence maps subject to a ranked list of constraints. Existing forms of FMO calculations are therefore time-consuming, often taking 10 to 20 minutes for typical prostate cases and much longer for more complex head/neck treatments. Thus, compute times often scale with the complexity of the plan and the numbers of the constraints. And this completes only the first step of a three-step process.

In various examples, generative machine learning models are adapted to perform FMO to produce fluence map values from input imaging data. The following examples thus identify ways in which an anatomy-dependent model of FMO parameters can be created and trained from a machine learning model. With use of a trained machine learning model, the FMO parameter calculation can be initialized closer to the end values for the parameters, reducing the time needed to compute a set of optimal fluence maps.

Additionally, in various examples, the following techniques perform FMO using machine learning models as part of a measurement, verification, or validation process or procedure. For instance, the results from a machine learning model can be used to provide an independent measure of an FMO program's performance outside of the specific physics and clinical information involved with a patient. Thus, machine learning models may provide or evaluate FMO data to serve as a benchmark for future radiotherapy plan development.

As a more detailed overview, the following outlines an FMO process, implemented with probabilistic machine learning models, that is performed in relation to VMAT radiotherapy planning. As discussed above, in VMAT treatments, multiple beams are directed toward the target, and each beam's cross-sectional shape conforms to the view of the target from that direction, or to a set of segments that all together provide a variable or modulated intensity pattern. Each beam is discretized into beamlets occupying the elements of a virtual rectangular grid in a plane normal to the beam. The dose is a linear function of beamlet intensities or fluence, as expressed with the following equation:

$$d_i(b) = \sum_{j=1}^{n} D_{ij} b_j \quad \text{(Equation 1)}$$

Where $d_i(b)$ is the dose deposited in voxel i from beamlet j with intensity $b_j$, and the vector of n beamlet weights is $b=(b_1, \ldots, b_n)^T$. $D_{ij}$ is the dose deposition matrix.

The FMO problem has been solved by multicriteria optimization. For instance, Romeijn et al. ("A unifying framework for multi-criteria fluence map optimization models," *Phys Med Biol* (49), 1991-2013, 2004) provided the following FMO model formulation:

$$(P): \min_{x \geq 0} F(d(b)) \quad \text{(Equation 2)}$$
$$\text{s.t.} \min_{x \geq 0} G_1(b) \leq C_1(b)$$
$$\ldots$$
$$\text{s.t.} \min_{x \geq 0} G_L(b) \leq C_L(b)$$

where $F(d(b))$ is a dose objective function, whose minimization is subject to the listed constraints and where the specialized objectives $G(b)$ are subject to dose constraints $C(b)$, and L is the number of constraints. The objective $F(d(b))$ minimizes the difference of the dose being calculated $d(b)$ with the prescribed dose $P(b)$:

$$F(d(b)) = \Sigma_i \|d_i(b) - P_i(b)\|_2^2 \quad \text{(Equation 3)}$$

where the sum is over all voxels. In such settings, solutions of constrained objectives may be achieved several ways. Pareto optimal solutions of multicriteria problems can be generated that have the property that improving any criterion value is only possible if the at least one other criterion value deteriorates, and that all the members of a Pareto optimal family of solutions lie on a Pareto boundary in solution space. By varying the relative weights of the constraints, the planner can move along through the optimal plans to explore the effects of the target dose versus organ sparing trade-offs.

An example of FMO operations is evidenced by iCycle or mCycle implementations; iCycle was originally implemented by researchers at Erasmus University Medical Center (Rotterdam, The Netherlands) and re-implemented as mCycle by Elekta Inc. (Stockholm, Sweden; and St. Charles, MO USA). iCycle and mCycle FMO performs beam angle and beam profile (fluence map) optimization based on a wish-list of prioritized objectives and constraints. Starting with an empty plan (no beams selected), optimal beam orientations are selected from predefined set of input directions. Iteration i starts with the selection of a candidate beam for the i-th orientation beam to be added to the plan. All orientations not yet selected are evaluated one-by-one solving for each of them a beam profile optimization for the trial i-th beam and all the previously-selected beams. Each iterative optimization satisfies all of the wishlist objectives and their constraints.

Figure 9:
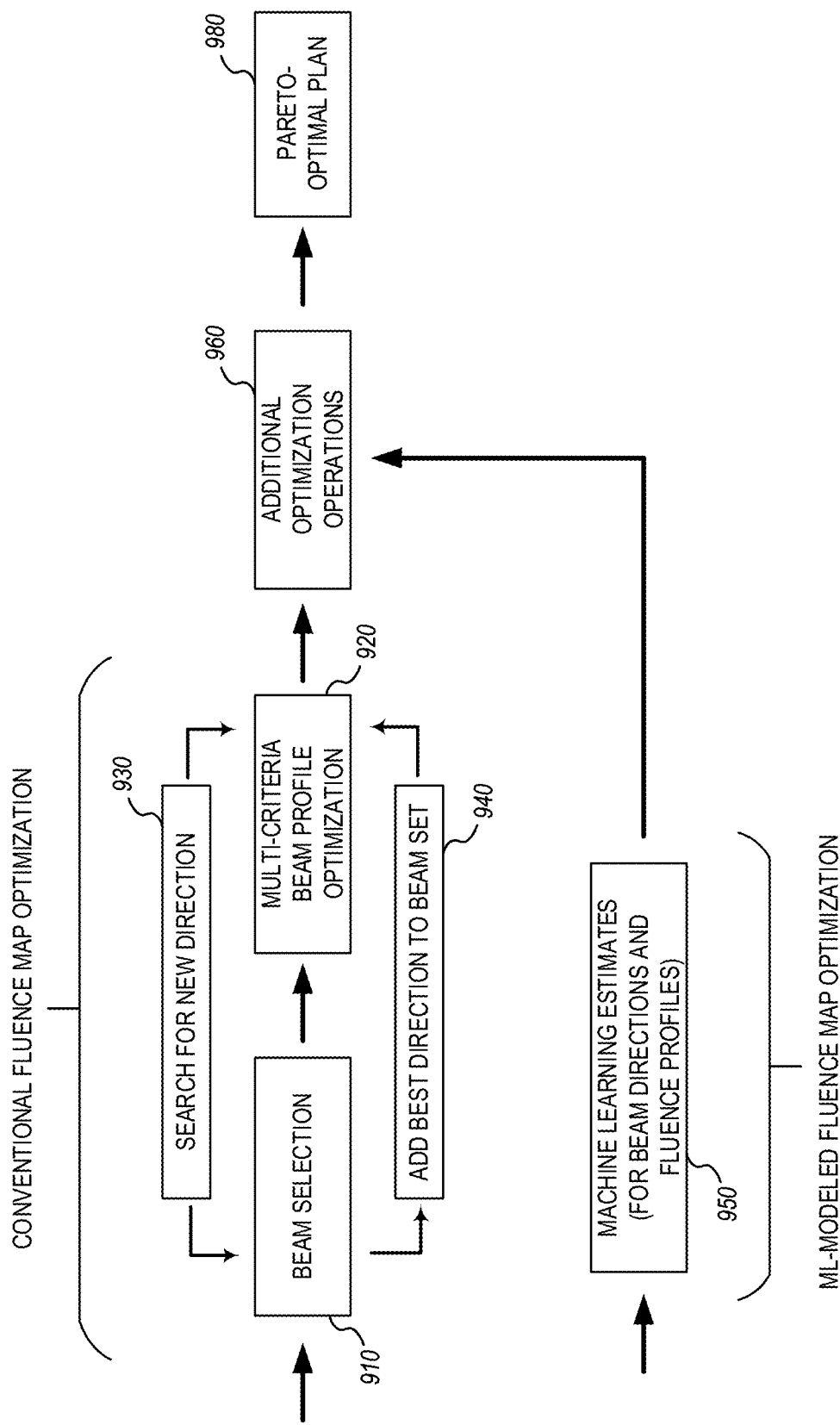
FIG. 9 illustrates an example of fluence map optimization operations, according to some examples.

FIG. 9 illustrates examples of FMO operations, providing a comparison of a conventional FMO process (such as performed by iCycle or mCycle) to a machine-learning-modeled FMO optimization performed with the various examples discussed herein. As shown, conventional FMO iterates through beam angle selection and profile optimization. Each iteration begins with the selection of a candidate beam orientation 910 added to the plan followed by multi-criterial optimization 920 of the beam profiles for the new beam and all previously-selected beams. The candidate beam with the best score, representing a best direction 940, is added to the plan. The first optimization stage is complete when additional beams, identified in a search for a new direction 930, fail to improve the optimization score sufficiently. A second optimization stage 960 is performed to improve the objectives further if possible. The result of this iterative build-up of beams and profiles is a plan 980 that is Pareto-optimal with respect to the wishlist objectives and constraints.

In contrast, the machine learning-modeled FMO techniques discussed below begins with an estimate of the beam directions and fluence profiles 950 learned from a population of clinical plans. This "plan estimate" directly goes to the second optimization stage 960 for refinement with respect to the wishlist objectives. This avoids the time-consuming buildup of searching performed by the first optimization stage and achieves shorter times to plan creation, because the machine learning estimate starts closer to the pareto optimum in parameter space than the conventional FMO initialization parameters.

For each iterative beam addition, the target and OAR objectives goals are guided by a wishlist, which provides a prioritized schedule of hard constraints and optimization objectives similar to those in Equation (2), above. For example, a wishlist for prostate radiotherapy may include hard constraints (e.g., specifying maximum radiation limits on planning target volume (PTV) areas, anatomical structures such as the rectum, bladder, etc.) and objectives (prioritized goal treatments on PTV areas, anatomical structures such as the rectum, bladder, etc.). In an example, the wishlist objectives are optimized one at a time in a multicriteria optimization. The highest priority objectives are the prescribed dose to the targets and the dose limits to the most vulnerable OARs. The lower-priority objectives provide additional constraints to achieve the highest therapeutic value possible. At each step, the prior optima serve as initial points and prior constraints for succeeding constraints' optimizations. Further, hard constraints may be defined to have the highest priority and include hard limits (that cannot be exceeded) on target areas (PTVs) and the major OARs. Objectives are goals that are attained (if possible) by repeated numerical optimization of the fluence maps.

In iCycle and mCycle implementations, target dose is optimized by minimizing the logarithmic tumor control probability (LTCP), $$LTCP = \frac{1}{V}\sum_{i \in V} e^{-\alpha(d_i(b) - P_i(b))} \quad \text{(Equation 4)}$$

that penalizes underdosage but permits the PTV to be affected by nearby OARs. In this equation, V is the set of voxels comprising the target PTV and $d^P$ is the prescribed dose. $\alpha$ is the cell sensitivity parameter—higher $\alpha$ results in a fewer target voxels with low dose and therefore a higher fraction of the voxels receiving 95% of the prescribed dose (good PTV coverage). The generalized equivalent uniform dose (gEUD) is a second useful dose function applied to OARs:

$$gEUD = \left[\frac{1}{V}\sum_{i \in V}(d_i(b))^a\right]^{\frac{1}{a}} \quad \text{(Equation 5)}$$

where V here is the set of voxels in the relevant organ and a is a parameter that modulates the dose delivered to that organ.

The wishlist-directed multicriteria optimization actually occurs in two phases. In the first phase, objectives are minimized within the constraints, proceeding from the first objective to the last objective on the wishlist. After each objective minimization, and based on its result, the constraint for that objective becomes a new constraint for the succeeding, lower-priority objectives. Adding the newly-achieved constraints insures that the lower-priority optimizations do not degrade any higher-priority objectives. Consequently, the lower-priority objectives have more constraints than the higher objectives. At the end of the first phase, each objective with a defined goal has either attained a value equal to that goal (even if further minimization would have been possible), or attained a value higher than its goal if the minimization constraints prevented the optimization from reaching that goal.

In the second phase all objectives are re-minimized to their fullest extent. That means that first phase objectives, apart from the LTCP objectives, that could have been minimized further, now are minimized to the greatest extent permitted by relevant constraint set. LTCP objectives' minimizations are stopped at the defined sufficient value to leave more room for minimization of lower-priority objectives and not needlessly escalate dose.

The resulting FMO plan (e.g., the pareto-optimal plan 980) is in fact a three-dimensional array of a physical dose in the coordinate frame of the target anatomy. Given the anatomy, and an array of fixed beam directions, the resulting optimal dose distribution is fixed as well since the many layers of optimizations are deterministic, at least to the numerical precision of the computer. Therefore, a set of parameters defining an optimal 3D dose are the set of optimal beam directions and the optimal fluence maps, one per beam. Further, if the beams are limited to a fixed set of angles, the fluence maps alone would define the 3D dose distribution.

Figure 10:
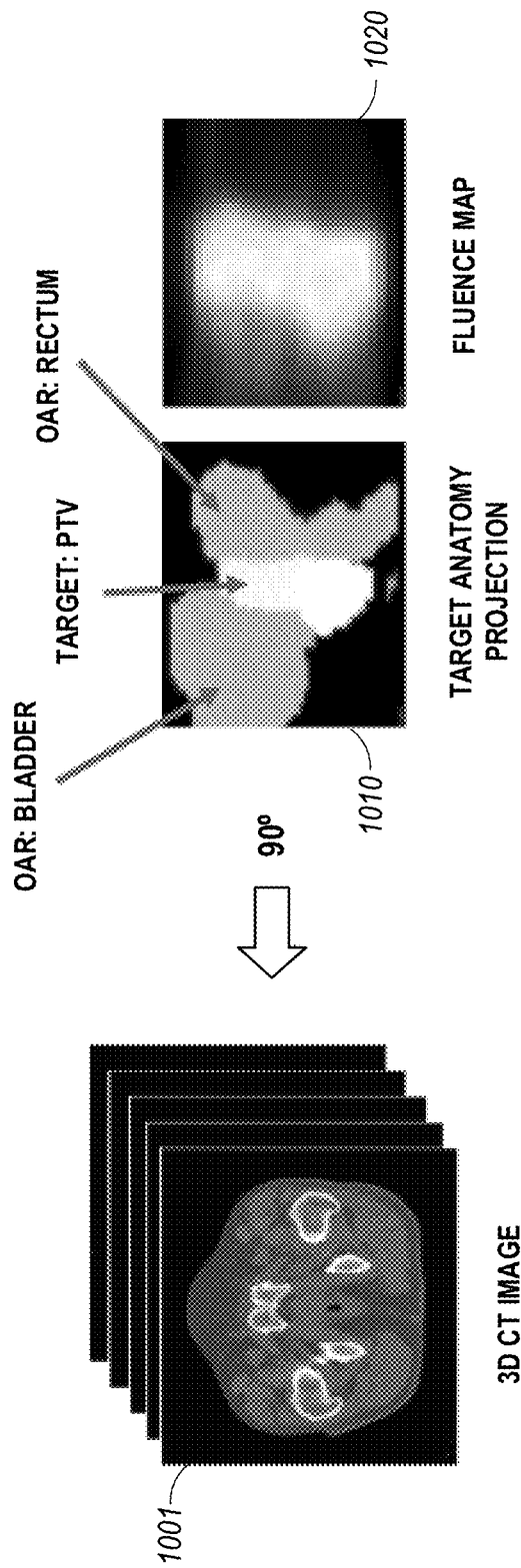
FIG. 10 illustrates an example of anatomical projection and fluence map images at a particular angle of a radiotherapy beam, according to some examples.

FIG. 10 depicts an example arrangement of the original patient imagery (provided in the 3D CT image set 1001), a projection image 1010 of the target anatomy at a 90° gantry angle, and a corresponding fluence map image 1020 of planned fluence at that same gantry angle. The projection image 1010 of the target anatomy specifically represents a target planning target volume (PTV) for treatment and the largest OARs as part of a prostate radiotherapy plan. The fluence map image 1020 specifically represents a 2D array of beamlet weights corresponding to rays through the fluence map pixels aimed at the target. The target anatomy projection image 1010 and the fluence map image 1020 are shown for one hypothetical beam at the gantry angle of 90°, but it will be understood that a VMAT treatment plan may have 100-150 beams at different angles, each with its own view of the target anatomy and fluence map.

In an example, various data formatting techniques are applied to training and inferencing fluence data within a machine learning model, to analyze the projection and fluence map image representations provided in FIG. 10. In practice, the anatomy and fluence or dose data exists in 3D rectilinear arrays. The FMO result, however, is the idealized 3D dose distribution corresponding to the optimal fluence maps. With the techniques discussed below, 2D fluence map representations can be produced at geometric planes normal to the beam (in coplanar treatments), in relationship to the linac and patient coordinate systems analogous to a beam's-eye-view projections of patient anatomy. Thus, anatomy and fluence maps may be represented as planar projections in a cylindrical coordinate system and used to train and draw inferences from the machine learning model for FMO.

Figure 11:
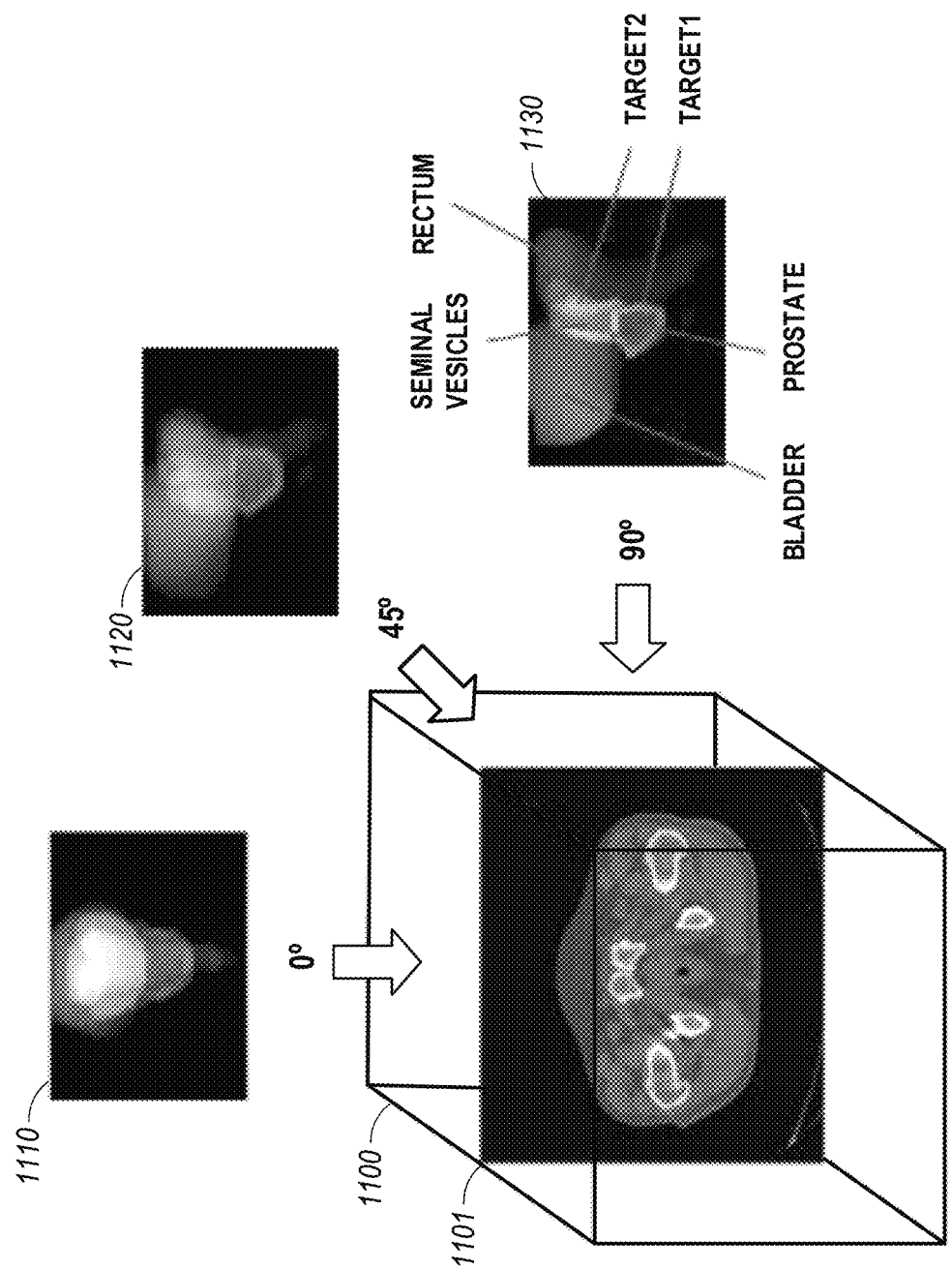
FIG. 11 illustrates an example of anatomical projections and radiotherapy treatment constraints at multiple angles of a radiotherapy treatment, according to some examples.

FIG. 11 first depicts the creation of multiple anatomy projections 1110, 1120, 1130 from a 3D volume of CT image data. An equivalent technique can be used to produce projections for MR images, and thus it will be understood that the following references to CT image data is provided for purposes of illustration and not limitation. As depicted in FIG. 11, multiple projections of the male pelvic organs are depicted relative to a 3D CT image 1101 of that anatomy, provided with views 1110, 1120, 1130 at 0, 45, and 90 degrees respectively (introduced earlier with respect to FIG. 2A). The patient orientation is head-first supine with the head of the patient beyond the top of the projections. The organs at risk (bladder, rectum), the target organs (prostate, seminal vesicles), and their encapsulating target volumes (Target1, Target2) are delineated (contoured) and each organ voxel was assigned a constant density value, and densities were summed for voxels in two or more structures.

Projection images through this anatomy about the central axis of the 3D CT volume 1100 and at the assigned densities may be obtained, for example, using a forward projection capability of the RTK cone beam CT reconstruction toolkit, an open-source cone-beam CT reconstruction toolkit based on the Insight Toolkit (ITK). In these views, the bladder at 0° is in front of the seminal vesicles (bladder is closest to the viewer) and rotates to the left in the next two views.

Figure 12:
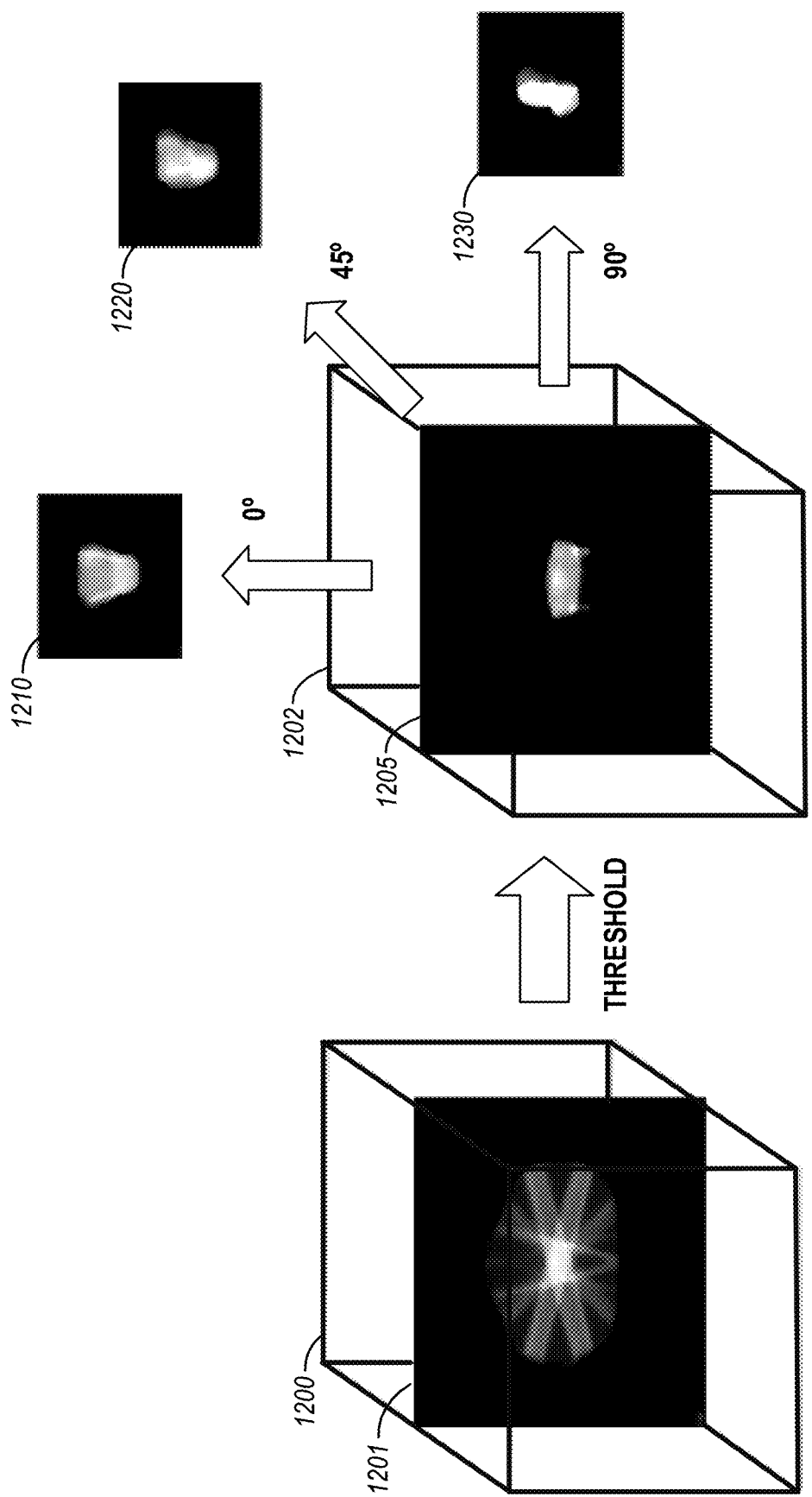
FIG. 12 illustrates an example of fluence map projections at multiple angles of a radiotherapy treatment, according to some examples.

FIG. 12 next depicts a set of equivalent-geometry fluence maps, corresponding to the views depicted in FIG. 11. As depicted, 2D fluence maps are produced from converting an FMO dose distribution volume 1200 into a thresholded volume 1202, as a dose distribution from radiotherapy beams (e.g., as depicted in a 2D dose distribution projection 1201), then the thresholded dose intensity (as shown in 1205) is converted into projection map-images (e.g., in 2D fluence map projections 1210, 1220, and 1230). For instance, projections from a 3D ideal fluence distribution may be established using the forward projection capability of the RTK cone beam CT reconstruction toolkit and the ITK toolkit. The produced projection views correspond to those views shown in FIG. 11: fluence map 1210 corresponding to 0-degree projection view 1110; fluence map 1220 corresponding to 45 degree projection view 1120; fluence map 1230 corresponding to 90 degree projection view 1130.

Figure 13:
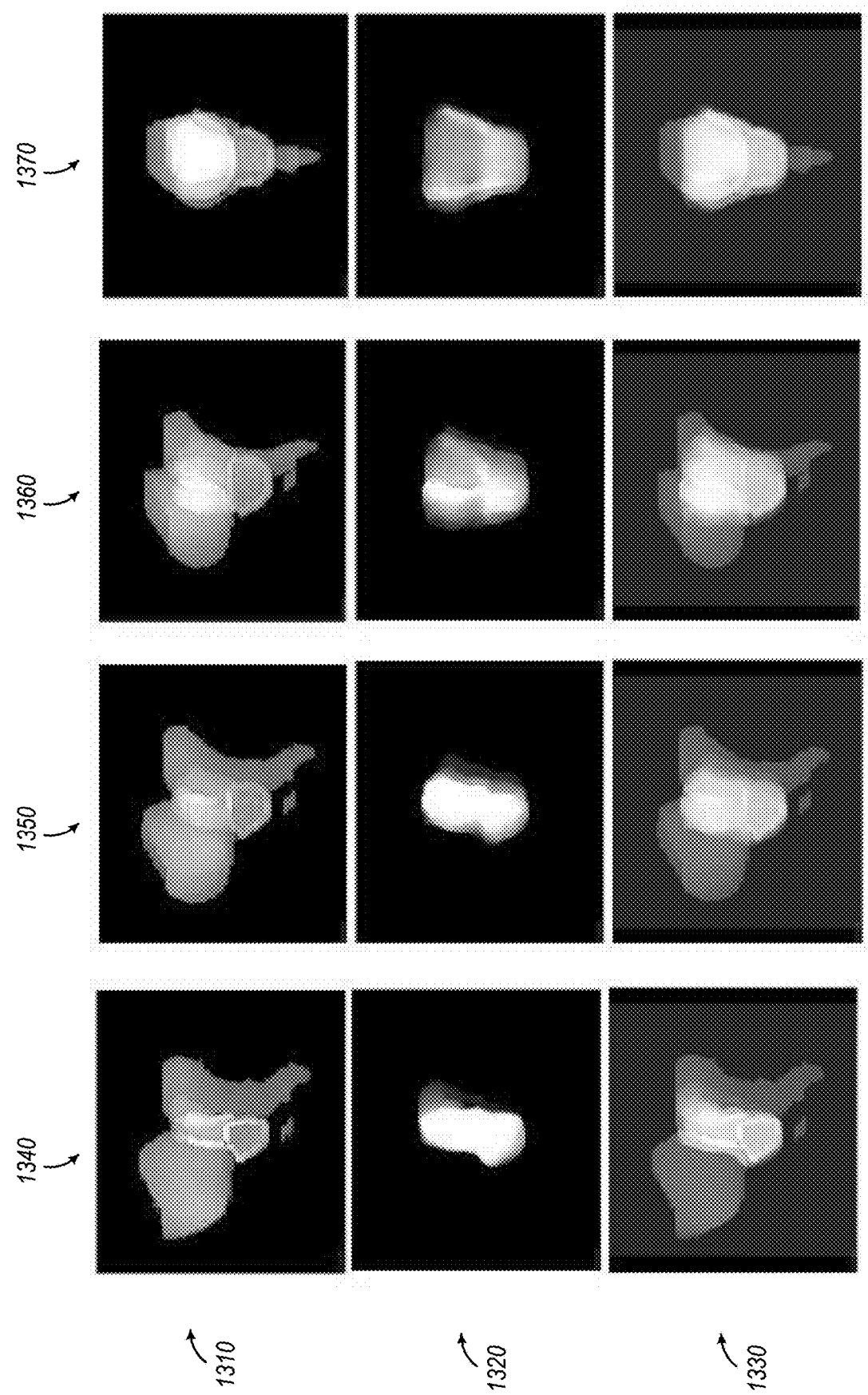
FIG. 13 illustrates pairings of anatomical projections, radiotherapy treatment constraints, and fluence map projections, at multiple angles of a radiotherapy treatment, according to some examples.

FIG. 13 further depicts, in each respective row, a set of 2D anatomy projections 1310, corresponding 2D fluence maps 1320, and superimposed 2D fluence maps 1330 that show fluence maps overlaid on anatomy projections. FIG. 13 further depicts, in each column, these projections and maps at linac gantry angles 90° (arrangement 1340), 120° (arrangement 1350), 150° (arrangement 1360), and 180° (arrangement 1370), respectively. Through the use of projection transformations, the 3D voxel data can be accurately be represented in a format compatible with the geometry of the treatment.

In various examples, these projections may be used for training machine learning models to produce a prediction of fluence map or plan parameters. Specifically, the following approaches discuss a trained machine learning model that predicts fluence map or plan parameters given only a new patient's images and relevant radiotherapy anatomy structures, such as OARs and treatment targets.

In an example, the prediction is made using probabilistic models of plans learned from populations of existing optimal fluence plans. The new patient data combined with the model enables a prediction of a fluence plan that serves as the starting point for direct aperture optimization. Among other benefits, this enables the time to refine the plan to clinical quality to be reduced.

The probabilistic models may be constructed as follows. Representing the anatomy data as a kind of random variable X, and the fluence plan information as random variable Y. Bayes' Rule states that the probability of predicting a plan Y given a patient X, p(Y|X), is proportional to the conditional probability of observing patient X given the training plans, Y, p(X|Y) and the prior probability of the training plans p(Y), or:

$$p(Y|X) \propto p(X|Y)p(Y) \qquad \text{(Equation 6)}$$

Bayesian inference predicts a plan Y* for a novel patient X* where the conditional probability p(Y*|X*) is drawn from the training posterior distribution p(Y|X). In practice, the novel anatomy X* is input to the trained network that then generates an estimate of the predicted plan Y* from the stored model p(Y|X).

Figure 14:
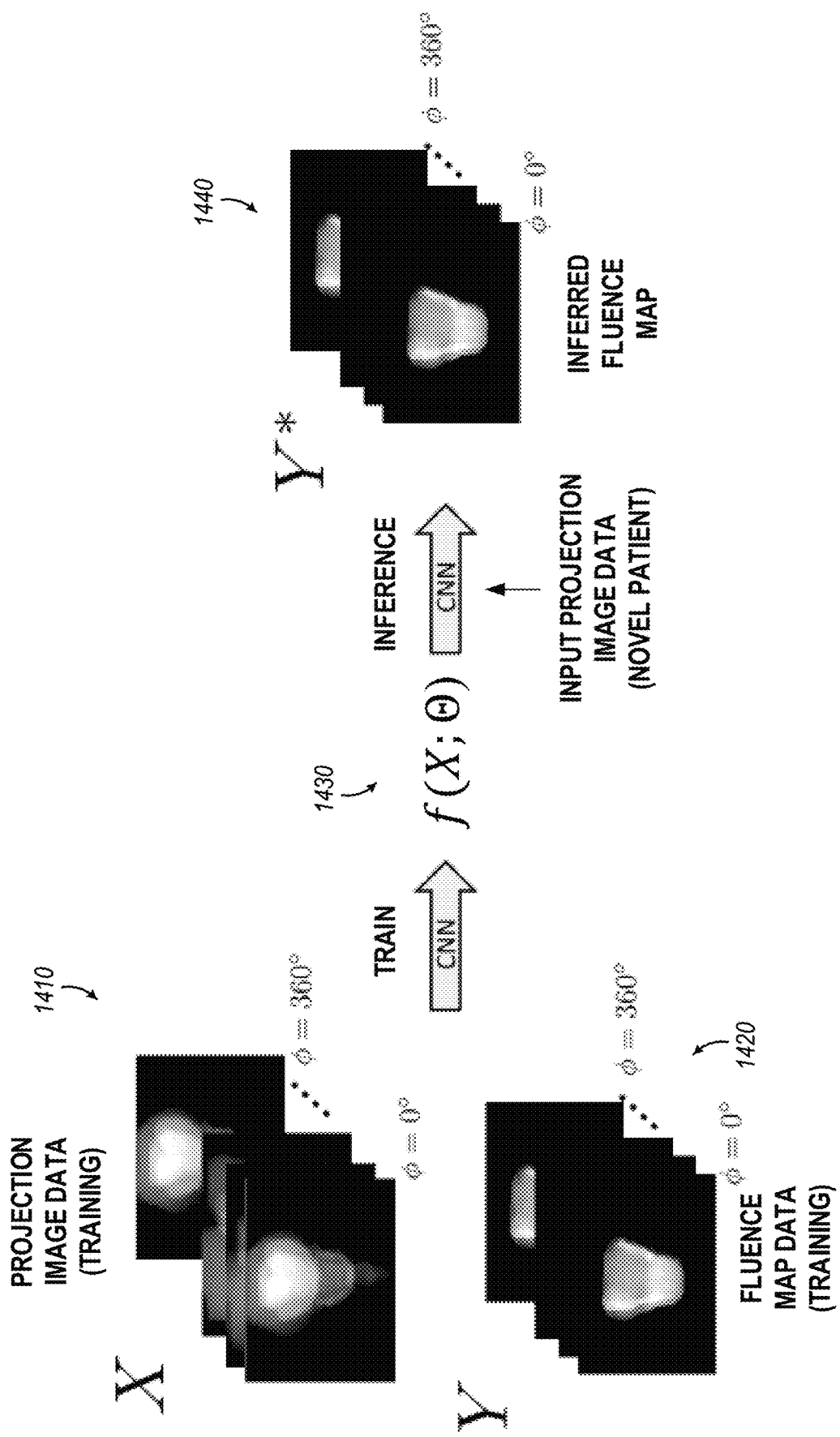
FIG. 14 illustrates a deep learning procedure to train a model to predict fluence maps from projection image data and fluence map data, according to some examples.

FIG. 14 depicts a schematic of the deep learning procedure to train a model to predict fluence maps. In an example, the training data includes pairs of 3D imaging projections 1410 and 3D stacks of fluence maps 1420 from the same data source (e.g., a same patient). Training produces the model $p(y|x)$ 1430 from which an estimate $\hat{y}$ can be inferred. The estimate is itself a 3D data volume 1440 with the same size and shape as the input anatomy and fluence data volumes. That estimate can be translated into a functional set of fluences and used as a warm start to accelerate FMO.

The plan posterior models p(Y|X) are built by training convolutional neural networks with pairs of known data (anatomy, plan; X, Y) in an optimization that minimizes network loss functions and simultaneously determines the values of the network layer parameters Θ. These neural network parameter values embed the posterior model p(Y|X) as p(Y|X; Θ). Once trained, the network can infer a plan for a new anatomy by the Bayes analysis described above. Neural network performance is established by comparing the inferred plans for test patients not used for training with those same test patients' original clinical plans—the better the neural network, the smaller the differences between the sets of plans.

In various examples, various forms of machine learning models may be implemented by artificial neural networks (NNs). At its simplest implementation, a NN consists of an input layer, a middle or hidden layer, and an output layer. Each layer consists of nodes that connect to more than one input node and connect to one or more output nodes. Each node outputs a function of the sum of its inputs $x = (x_1, \ldots, x_n)$, $y \sim \sigma(w^T x + \beta)$, where w is the vector of input node weights and β is the layer bias and the nonlinear function σ is typically a sigmoidal function. The parameters Θ=(w, β) are the realization of the model learned to represent the relationship Y=$f$(X; Θ). The number of input layer nodes typically equals the number of features for each of a set of objects being sorted into classes, and the number of output layer nodes is equal to the number of classes. For regression, the output layer typically has a single node that communicates the estimated or probable value of the parameter.

A network is trained by presenting it with object features where the object's class or parameter value is known and adjusting the node weights w and biases β to reduce the training error by working backward from the output layer to the input layer—an algorithm called backpropagation. The training error is a normed difference $\|y - f(x)\|$ between the true answer y and the inference estimate $f(x)$ at any stage of training. The trained network then performs inference (either classification or regression) by passing data forward from input to output layer, computing the nodal outputs $\sigma(w^T x + \beta)$ at each layer.

Neural networks have the capacity to discover general relationships between the data and classes or regression values, including non-linear functions with arbitrary complexity. This is relevant to the problem of radiotherapy dose prediction, or treatment machine parameter prediction, or plan modelling, since the shape or volume overlap relationships of targets and organs as captured in the dose-volume histogram and the overlap-volume histogram are highly non-linear and have been shown to be associated with dose distribution shape and plan quality.

Modern deep convolutional neural networks (CNNs) have many more layers (are much deeper) than early NNs—and may include dozens or hundreds of layers, each layer composed of thousands to hundreds of thousands of nodes, with the layers arranged in complex geometries. In addition, the convolution layers map isomorphically to images or any other data that can be represented as multi-dimensional arrays and can learn features embedded in the data without any prior specification or feature design. For example, convolution layers can locate edges in pictures, or temporal/pitch features in sound streams, and succeeding layers find larger structures composed of these primitives. In the past half-dozen years, some CNNs have approached human performance levels on canonical image classification tests—correctly classifying pictures into thousands of classes from a database of millions of images.

CNNs are trained to learn general mappings $f: X \rightarrow Y$ between data in source and target domains X, Y, respectively. Examples of X include images of patient anatomy or functions of anatomy conveying structural information. Examples of Y could include maps of radiation fluence or delivered dose, or maps of machine parameters superposed onto the target anatomy X. As indicated in FIG. 14, pairs of matched, known X, Y data may be used to train a CNN. The CNN learns a mapping or function $f(X; \Theta)$ of both anatomy and network parameters $\Theta = (\theta_1, \ldots, \theta_n)^T$ where $\theta_i = \{w_i, \beta_i\}$ are the parameters for the i-th layer. Training minimizes a loss function $\mathcal{L}(\Theta)$ over the mapping $f$ and a ground truth or reference plan parameter $\hat{Y}$ $$\mathcal{L}(\theta^*) = \operatorname*{argmin}_{\Theta} [\|f(X; \Theta) - \hat{Y}\|_K + \lambda \|\Theta\|_L], \quad \text{(Equation 7)}$$
$$K, L \in \{1, 2\}$$

where the first term minimizes the difference between the network estimated target $f(X; \Theta)$ and the reference plan parameter $\hat{Y}$ and the second term minimizes the variation of the values of the $\Theta$. Subscripts K,L specify the norm. The L2 norm (K, L=2) is globally convex but produces blurred estimates of Y while the L1 norm (K, L=1) encourage sharper estimates. Network performance typically dictates what combination of norms are useful.

Figure 15A:
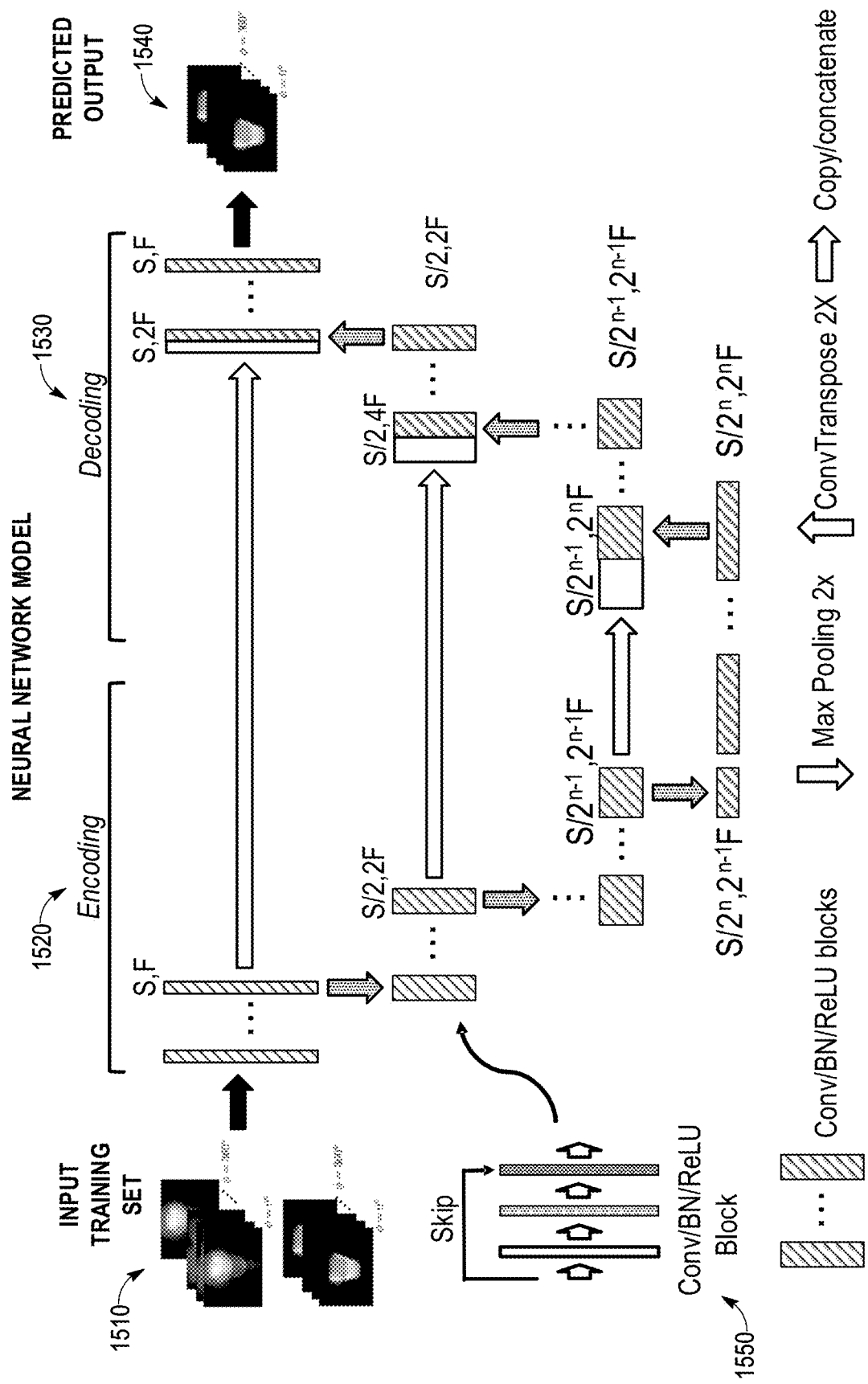
FIGS. 15A and 15B respectively depict a schematic of generative and discriminative deep convolutional neural networks used in predicting fluence map representations, according to some examples.

FIG. 15A depicts a schematic of a U-Net deep convolutional neural network (CNN). Specifically, this schematic depicts the U-Net deep CNN model adapted for generating a fluence map representation in a generative arrangement, such as to provide a generative model adapted for the techniques discussed herein. Shown are a pair of input images representing target anatomy constraints (top image) and a radiotherapy treatment X-ray fluence representation corresponding to that target anatomy (bottom image), provided in an input training set 1510 to train the network. The output is a predicted fluence map representation 1540, inferred for a target image. The input training set 1510 may include individual pairs of input images that are projected from a 3D anatomy imaging volume and 3D fluence volume; these individual pairs of input images may comprise individual images that are projected at relevant beam angle used for treatment with a radiotherapy machine. The output data set, provided in the fluence map representation 1540, is a representation that may comprise individual output images or a 3D fluence volume.

A U-Net CNN creates scaled versions of the input data arrays on the encoding side by max pooling and re-combines the scaled data with learned features at increasing scales by transposed convolution on the encoding side to achieve high performance inference. The black rectangular blocks represent combinations of convolution/batch normalization/rectified linear unit (ReLU) layers; two or more are used at each scale level. The blocks' vertical dimension corresponds to the image scale (S) and the horizontal dimension is proportional to the number of convolution filters (F) at that scale. Equation 7 above is a typical U-Net loss function.

The model shown in FIG. 15A depicts an arrangement adapted for generating an output data set (output fluence map representation images 1540) based on an input training set 1510 (e.g., paired anatomy images and fluence map representation images). The name derives from the "U" configuration, and as is well understood, this form of CNN model can produce pixel-wise classification or regression results. In some cases, a first path leading to the CNN model includes one or more deformable offset layers and one or more convolution layers including convolution, batch normalization, and an activation such as the rectified linear unit (ReLU) or one of its variants.

The left side of the model operations (the "encoding" operations 1520) learns a set of features that the right side (the "decoding" operations 1530) uses to reconstruct an output result. The U-Net has n levels consisting of conv/BN/ReLU (convolution/batch normalization/rectified linear units) blocks 1550, and each block has a skip connection to implement residual learning. The block sizes are denoted in FIG. 15A by "S" and "F" numbers; input images are S×S in size, and the number of feature layers is equal to F. The output of each block is a pattern of feature responses in arrays the same size as the images.

Proceeding down the encoding path, the size of the blocks decreases by ½ or $2^{-1}$ at each level while the size of the features by convention increases by a factor of 2. The decoding side of the network goes back up in scale from S/2" while adding in feature content from the left side at the same level; this is the copy/concatenate data communication. The differences between the output image and the training version of that image drives the generator network weight adjustments by backpropagation. For inference, or testing, with use of the model, the input would be a single projection image or collection of multiple projection images of radiotherapy treatment constraints (e.g., at different beam or gantry angles) and the output would be graphical fluence map representation images 1540 (e.g., one or multiple graphical images corresponding to the different beam or gantry angles).

Figure 15B:
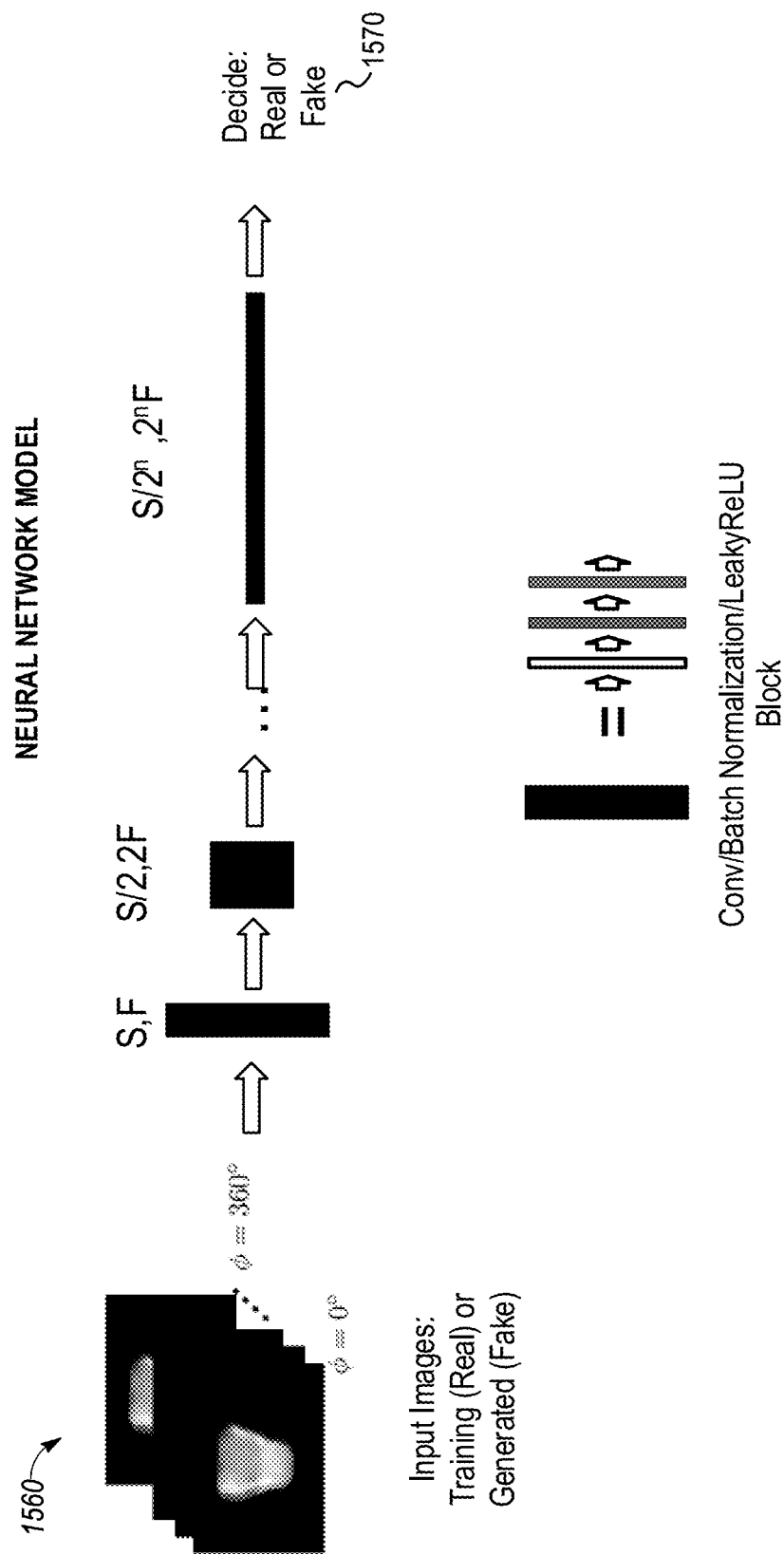

The representation of the model of FIG. 15A specifically illustrates the training and prediction of a generative model, which is adapted to perform regression rather than classification. FIG. 15B illustrates an exemplary CNN model adapted for discriminating a synthetic fluence map representation(s) according to the present disclosure. As used herein, a "synthetic" image refers to a model-generated image, and thus "synthetic" is used interchangeably herein with the terms "estimated", "computer-simulated", or "computer-generated". The discriminator network shown in FIG. 15B may include several levels of blocks configured with stride-2 convolutional layers, batch normalization layers and ReLU layers, and separated pooling layers. At the end of the network, there will be one or a few fully connected layers to form a 2D patch for discrimination purposes. The discriminator shown in FIG. 15B may be a patch-based discriminator configured to receive input synthetic fluence map representation images 1560 (e.g., generated from the generator shown in FIG. 15A), classify the image as real or fake, and provide the classification as output detection results 1570.

In an example, the present FMO modeling techniques may be generated using a specific a type of CNN, generative adversarial networks (GANs), to predict fluence plan parameters (a fluence map) from radiotherapy treatment constraints of new patient anatomy. In a further example, a cycle-consistent GAN may be used to predict fluence plan parameters from new patient anatomy. The following provides an overview of relevant GAN technologies.

Generative adversarial networks are generative models (generate probability distributions) that learn a mapping from random noise vector z to output image y as G: z→y. Conditional adversarial networks learn a mapping from observed image x and random noise z as G: {x, z}→y. Both adversarial networks consist of two networks: a discriminator (D) and a generator (G). The generator G is trained to produce outputs that cannot be distinguished from "real" or actual training images by an adversarial trained discriminator D that is trained to be maximally accurate at detecting "fakes" or outputs of G.

The conditional GAN differs from the unconditional GAN in that both discriminator and generator inferences are conditioned on an example image of the type X in the discussion above. The conditional GAN loss function is expressed as:

$$\mathcal{L}_{cGAN}(G,D) = \mathbb{E}_{x,y \sim p_{data}(x,y)}[\log(D(x,y))]$$

$$E_{x \sim p_{data}(x), z \sim p_z(z)}[\log(1-D(x,G(x,z)))] \quad \text{(Equation 8)}$$

where G tries to minimize this loss against an adversarial D that tries to maximize it, or, $$G^* = \arg\min_G \max_D \mathcal{L}_{cGAN}(G, D) \quad \text{(Equation 9)}$$

In addition, one wants the generator G to minimize the difference between the training estimates and the actual training ground truth images, $$\mathcal{L}_{L1}(G) = \mathbb{E}_{x,y \sim p_{data}(x,y), z \sim p_z(z)}[\|-G(x,z)\|_1] \quad \text{(Equation 10)}$$

so, the complete loss is the λ-weighted sum of two losses:

$$G^* = \arg\min_G \max_D \mathcal{L}_{cGAN}(G, D) + \lambda \mathcal{L}_{L1}(G) \quad \text{(Equation 11)}$$

In an example, the generator in the conditional GAN may be a U-Net.

Consistent with examples of the present disclosure, the treatment modeling methods, systems, devices, and/or processes based on such models include two stages: training of the generative model, with use of a discriminator/generator pair in a GAN; and prediction with the generative model, with use of a GAN-trained generator. Various examples involving a GAN and a CycleGAN for generating fluence map representation images are discussed in detail in the following examples. It will be understood that other variations and combinations of the type of deep learning model and other neural-network processing approaches may also be implemented with the present techniques. Further, although the present examples are discussed with reference to images and image data, it will be understood that the following networks and GAN may operate with use of other non-image data representations and formats.

Figure 16A:
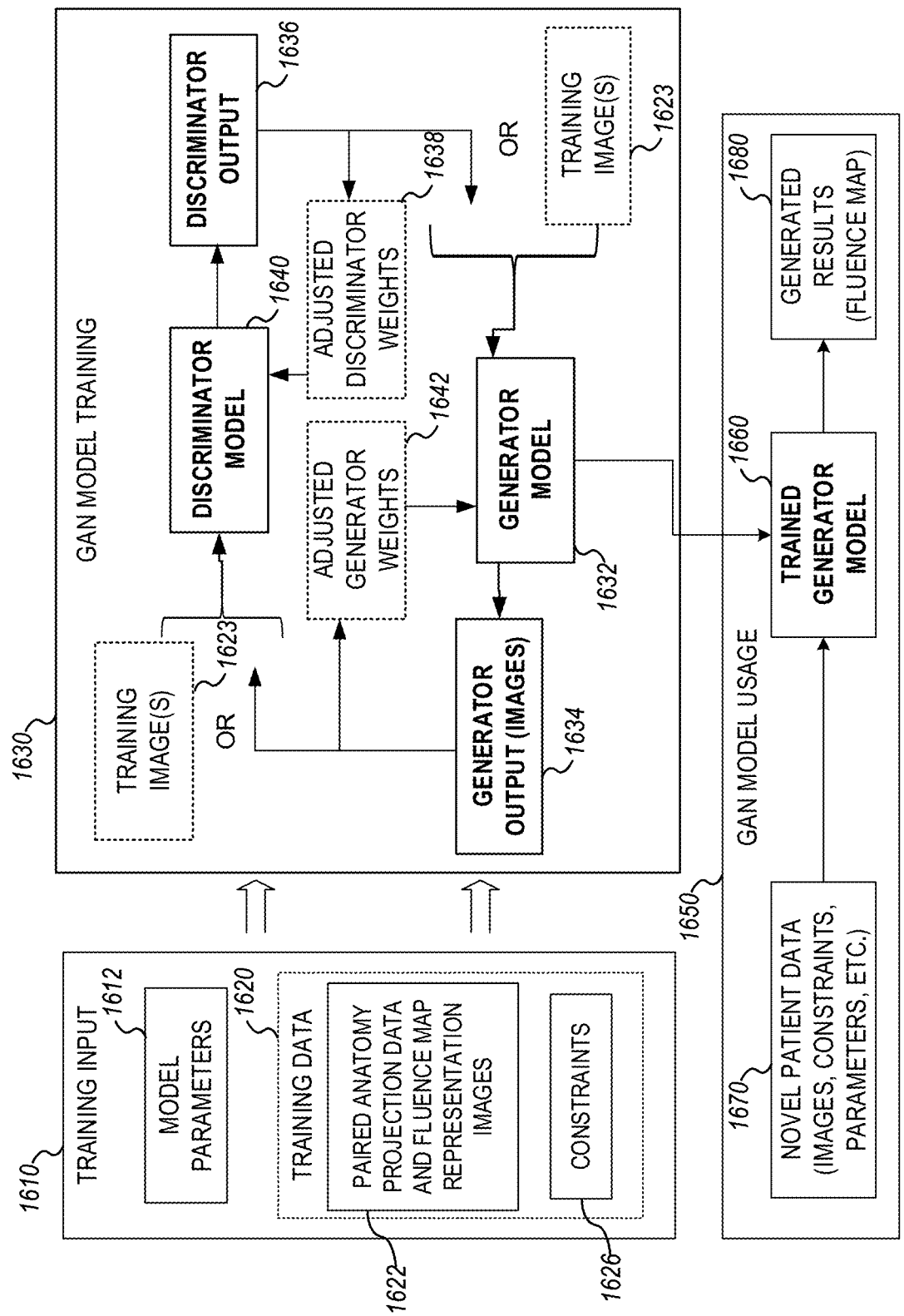
FIGS. 16A and 16B respectively depict schematics of a generative adversarial network and a cycle-consistent generative adversarial network used for training a generative model for predicting fluence map representations, according to some examples.

FIG. 16A illustrates a data flow for training and use of a GAN adapted for generating a fluence plan parameters (a fluence map representation) from a received set of projection images that represents a view of an anatomy of a subject image. For instance, the generator model 1632 of FIG. 16A, which is trained to produce a trained generator model 1660, may be trained to implement the processing functionality provided as part of the image processor 114 in the radiotherapy system 100 of FIG. 1.

Accordingly, a data flow of the GAN model usage 1650 (prediction or inference) is depicted in FIG. 16A as the provision of new patient data 1670 (e.g., a projection image that represents radiotherapy treatment constraints in a view of an anatomy of a subject input images from a novel patient) to a trained generator model 1660, and the use of the trained generator model 1660 to produce a prediction or estimate of a generator output (images) 1634 (e.g., synthetic graphical fluence map representation images corresponding to the input projection image that represents a view of an anatomy of a subject image). A projection image can be generated from one or more CT or MR images of a patient anatomy representing a view of the anatomy from a given beam position (e.g., at an angle of the gantry) or other defined positions.

GANs comprise two networks: a generative network (e.g., generator model 1632) that is trained to perform classification or regression, and a discriminative network (e.g., discriminator model 1640) that samples the generative network's output distribution (e.g., generator output (images) 1634) or a training fluence map representation image from the training images 1623 and decides whether that sample is the same or different from the true test distribution. The goal for this system of networks is to drive the generator network to learn the ground truth model as accurately as possible such that the discriminator net can only determine the correct origin for generator samples with 50% chance, which reaches an equilibrium with the generator network. The discriminator can access the ground truth but the generator only accesses the training data through the response of the detector to the generator's output.

The data flow of FIG. 16A also illustrates the receipt of training input 1610, including various values of model parameters 1612 and training data 1620 (with such training images 1623 including a set of projection images that represent different views of an anatomy of subject patient imaging data paired with real graphical fluence map representations corresponding to the patient imaging data at the different views, and conditions or constraints 1626. These conditions or constraints 1626 (e.g., one or more radiotherapy treatment target areas, one or more organs at risk areas, etc.) may be indicated directly in the anatomy images themselves (e.g., as shown with projection image 1010), or provided or extracted as a separate data set. The training input 1610 is provided to the GAN model training 1630 to produce a trained generator model 1660 used in the GAN model usage 1650.

As part of the GAN model training 1630, the generator model 1632 is trained on real training fluence map representation images and corresponding training projection images that represent views of an anatomy of a subject image pairs 1622 (also depicted in FIG. 16A as 1623), to produce and map segment pairs in the CNN. In this fashion, the generator model 1632 is trained to produce, as generator output (images) 1634, computer-simulated (estimated or synthetic) images of fluence map representations and fluence values based on an input map. The discriminator model 1640 decides whether a simulated fluence map representation image or images is from the training data (e.g., the training or true fluence map representation images) or from the generator (e.g., the estimated or synthetic fluence map representation images), as communicated between the generator model 1632 and the discriminator model 1640. The discriminator output 1636 is a decision of the discriminator model 1640 indicating whether the received image is a simulated image or a true image and is used to train the generator model 1632. In some cases, the generator model 1632 is trained utilizing the discriminator on the generated images and is further trained based on cycle-consistency loss information. This training process results in backpropagation of weight adjustments 1638, 1642 to improve the generator model 1632 and the discriminator model 1640.

During training of generator model 1632, a batch of training data can be selected from the patient images (indicating radiotherapy treatment constraints) and expected results (fluence map representations). The selected training data can include at least one projection image of patient anatomy representing a view of the patient anatomy from a given beam/gantry angle and the corresponding training or real fluence map representations image at that given beam/gantry angle. The selected training data can include multiple projection images of patient anatomy representing views of the same patient anatomy from multiple equally spaced or non-equally spaced angles (e.g., at gantry angles, such as from 0 degrees, from 15 degrees, from 45 degrees, from 60 degrees, from 75 degrees, from 90 degrees, from 105 degrees, from 120 degrees, from 135 degrees, from 150 degrees, from 165 degrees, from 180 degrees, from 195 degrees, from 210 degrees, from 225 degrees, from 240 degrees, from 255 degrees, from 270 degrees, from 285 degrees, from 300 degrees, from 315 degrees, from 330 degrees, from 345 degrees, and/or from 360 degrees) and the corresponding training fluence map representation image and/or machine parameter data at those different equally-spaced or non-equally spaced gantry angles.

Thus, in this example, data preparation for the GAN model training 1630 requires fluence map representation images that are paired with projection images that represent views of an anatomy of subject images (these may be referred to as training projection images that represent a view of an anatomy of a subject image at various beam/gantry angles). Namely, the training data includes paired sets of fluence map representation images at the same gantry angles as the corresponding projection images. In an example, the original data includes pairs of projection images that represents a view of an anatomy of a subject at various beam/gantry angles and corresponding fluence map representations of fluence at the corresponding beam/gantry angles that may be registered and resampled to a common coordinate frame to produce pairs of anatomy-derived images. The training data can include multiple of these paired images for multiple patients at any number of different beam/gantry angles. In some cases, the training data can include 360 pairs of projection images and fluence map representation images, one for each angle of the gantry for each training patient.

The expected results can include estimated or synthetic graphical fluence map representations of fluence outcomes, that can be further optimized and converted into control points. Such control points may be converted and optimized into control points for generating a beam shape at the corresponding beam/gantry angle to define the delivery of radiation treatment to a patient. The control points or machine parameters can include at least one beam/gantry angle, at least one multi-leaf collimator leaf position, and at least one aperture weight or intensity, based on the specifications of the fluence map.

In detail, in a GAN model, the generator (e.g., generator model 1632) learns a distribution over the data x, $p_G(x)$, starting with noise input with distribution $p_Z(z)$ as the generator learns a mapping G (z; $\theta_G$): $p_Z(z) \rightarrow p_G(x)$ where G is a differentiable function representing a neural network with layer weight and bias parameters $\theta_G$. The discriminator, D(x; $\theta_D$) (e.g., discriminator model 1640), maps the generator output to a binary scalar {true, false}, deciding true if the generator output is from actual data distribution $p_{data}(x)$ and false if from the generator distribution $p_G(x)$. That is, D(x) is the probability that x came from $p_{data}(x)$ rather than from $p_G(x)$. In another example, paired training data may be utilized in which, for instance, Y is conditioned (dependent) on X. In such cases, the GAN generator mapping is represented by G(y|x; $\theta_G$): X→Y from data domain X where data x∈X represents the anatomy projection images and domain Y where data y∈Y represents the fluence map representation values corresponding to x. Here an estimate for an fluence map representation value is conditioned on its projection. Another difference from the straight GAN is that instead of a random noise z input, the projection image x is the generator input. For this example, the setup of the discriminator is the same as above. In general, the generator model 1632 and the discriminator model 1640 are in a circular data flow, where the results of one feed into the other. The discriminator takes either training or generated images and its output is used to both adjust the discriminator weights and to guide the training of the generator network.

Figure 16B:
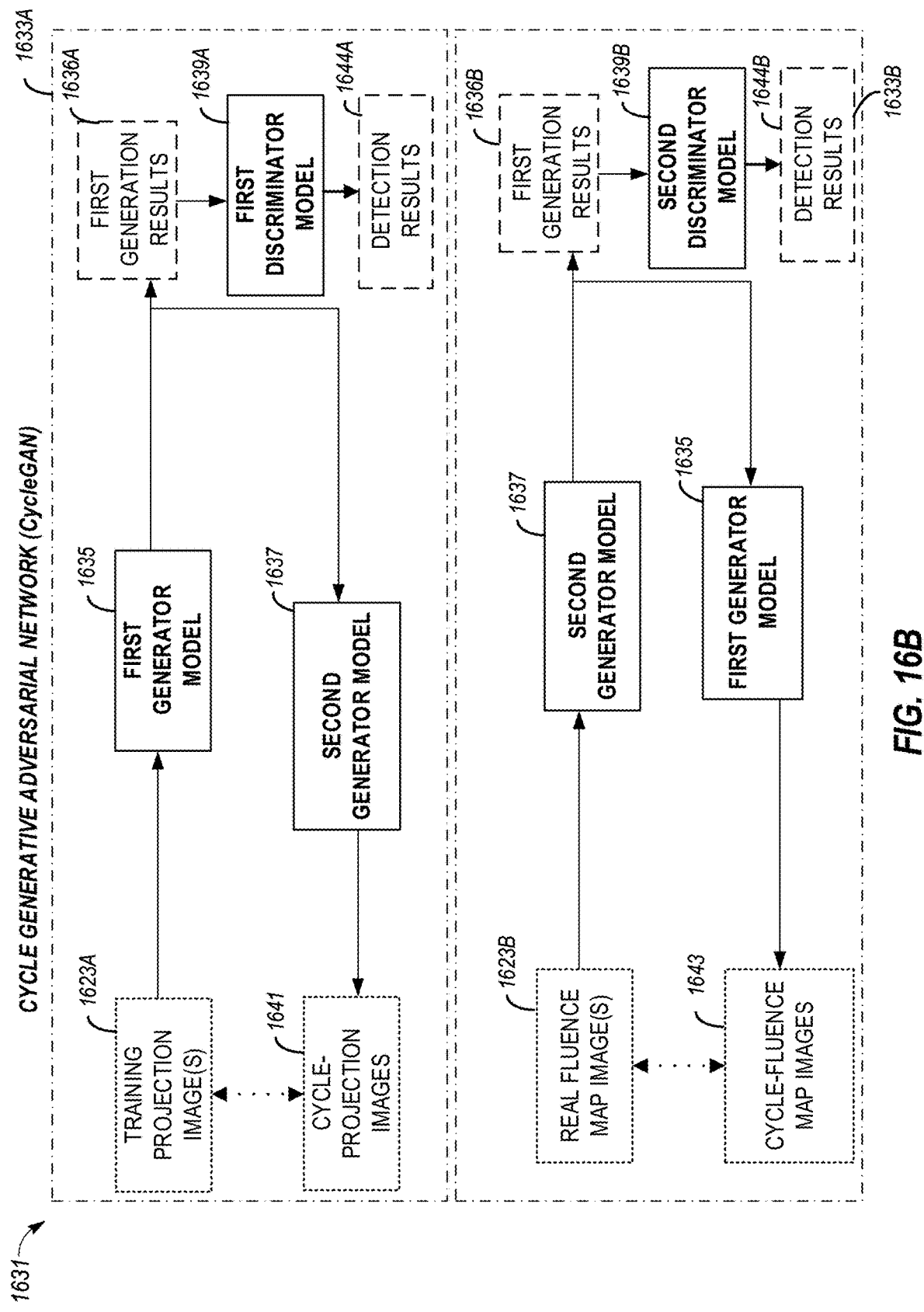

Another useful extension of a GAN is the CycleGAN, which is described below in connection with FIG. 16B. FIG. 16B illustrates training and use of CycleGAN 1631 for generating a collection of fluence map representation images (e.g., a collection of synthetic or estimated fluence map representation images, projected at radiotherapy beam angles) from a received collection of projection images (e.g., a collection of projection images of anatomy indicating radiotherapy treatment constraints, projected at the radiotherapy beam angles) according to some examples of the disclosure. CycleGAN 1631 includes a first generator model 1635, second generator model 1637, a first discriminator model 1639A, and a second discriminator model 1639B. The first generator model 1635 includes deformable offset layers and convolution blocks and the second generator model 1637 includes deformable offset layers and convolution blocks. These two models 1635 and 1637 may each be an implementation of generator model 1632 (e.g., in FIG. 16A, as regression-type DCNN models), and first discriminator model 1639A and second discriminator model 1639B may each be an implementation of discriminator model 1640 (e.g., as classification-type DCNN models). CycleGAN 1631 may be divided into two portions, first portion 1633A and second portion 1633B.

The convolution blocks of each generator model 1635 and 1637 may be trained together or separate from training of the other generator and discriminator models. Specifically, the convolution blocks of the generator models 1635 and 1637 are trained to obtain the correct weights to perform their function. The deformable offset layers may each be trained to coordinate offsets, resample, and perform interpolation. The deformable offset layers may be trained together or separate from training of the generator and discriminator models. The effect of these offset layers changes the original regular sampling grids from upper convolutional blocks, introduces coordinate offsets, and resamples the images using interpolation. The deformable offset layers may alternatively or in addition be implemented using a spatial transformer, other types of convolutional layers, and/or any other module that can store deformed structure information for an image. The number of offset layers in the deformable offset layers may vary based on image size, the number of down-sampling convolutional layers, and other factors.

In an example, in first portion 1633A, the first generator model 1635 may be trained to receive a training collection of projection images 1623A (which may include anatomical projection images, one of image pairs 1622) and generate a respective synthetic first collection of fluence map representation images as first generation results 1636A. The first generator model 1635 is referred to as $G^{proj2fluence}$.

First generation results 1636A may be provided to the first discriminator model 1639A. The first discriminator model 1639A may classify the synthetic collection of fluence map representation images as a real collection of fluence map representation training images or a simulated collection of fluence map representation training images and provide the classification as detection results 1644A. The first generation results 1636A and detection results 1644A may be fed back to the first generator model 1635 and first discriminator model 1639A to adjust weights implemented by the first generator model 1635 and first discriminator model 1639A. For example, first generation result 1636A (e.g., a collection of fluence map representation images generated by first generator model 1635) and detection results 1644A may be used to calculate adversarial losses.

The first generation results 1636A (e.g., the synthetic collection of fluence map representation images) may also be concurrently provided to the second generator model 1637. The second generator model 1637 may receive first generation results 1636A and generate a respective simulated collection of anatomical projection images as outputs. The simulated collection of anatomical projection images may be referred to as a cycle collection of anatomical projection images 1641 and may be used to compute cycle losses to adjust weights of first/second generator model 1635/1637. The second generator model 1637 that generates the first cycle collection of anatomical projection images 1641 is referred to as $G^{fluence2proj}$.

In an example, in the second portion 1633B, the second generator model 1637 may be trained to receive a real collection of training fluence map representation images 1623B (which may include one of image pairs 1622) and to generate a respective synthetic collection of anatomical projection images (a synthetic or simulated collection of anatomical projection images) as first generation results 1636B. The second generator model 1637 that generates the first generation results 1636B is the same generator as that used in the first portion 1633A.

First generation results 1636B may be provided to the second discriminator model 1639B. The second discriminator model 1639B may classify the synthetic collection of anatomical projection images as a real collection of anatomical projection training images or a simulated collection of anatomical projection training images and provide the classification as detection results 1644B. The first generation results 1636B and detection results 1644B may be fed back to the second generator model 1637 and the second discriminator model 1639B to adjust weights implemented by second generator model 1637 and second discriminator model 1639B. For example, first generation result 1636B (e.g., a synthetic collection of anatomical projection images generated by second generator model 1637) and the detection results 1644B may be used to calculate adversarial losses.

First generation results 1636B (e.g., synthetic collection of anatomical projection images) may also be concurrently provided to the first generator model 1635. The first generator model 1635 may receive first generation results 1636B and generate respective cycle-fluence map representation images 1643 as outputs. The cycle-fluence map representation images 1643 may be used to compute cycle losses to adjust weights of first/second generator model 1635/1637. The first generator model 1635 that generates the cycle-fluence map representation images 1643 is the same generator as that used in the first portion 1633A, and the second generator model 1637 that generates the cycle-fluence map representation images 1643 is the same generator as that used in the first portion 1633A.

In some examples, "adversarial losses" may account for the classification losses for the first and second discriminator models 1639A and 1639B. First and second discriminator models 1639A and 1639B may classify whether the synthetic images have similar distribution as true images or not. For cycle-consistency losses, the losses are calculated between each pair of true collection of projection images and cycle-collection of projection images, and each pair of true fluence map representation images and cycle-fluence map representation images, respectively. For example, a first loss may be calculated between a collection of projection training images 1623A and cycle-collection of projection images 1641 and a second loss may be calculated between real training collection of fluence map representation images 1623B and collection of cycle-fluence map representation images 1643. The cycle-collection of projection images 1641 and cycle-fluence map representation images 1643 may both be obtained by doing forward and backward cycles. Each pair of true collection of projection images 1623A and cycle-collection of projection images 1641 may be in the same collection of projection images domain, and each pair of real training fluence map representation images 1623B and cycle-fluence map representation images 1643 may be in the same graphical fluence map representation image domain. The CycleGAN 1631 may accordingly rely on a whole pool (or a plurality) of true or real projection training images 1623A and a whole pool (or a plurality) of real training fluence map representation images 1623B to produce synthetic fluence map representation images (collection of fluence map representation images), synthetic collection of projection images, cycle-collection of projection images 1641, and cycle-fluence map representation images 1643. Based on "adversarial losses" and "cycle-consistency losses," CycleGAN 1631 may produce sharp synthetic fluence map representation images, which have similar image resolution as real fluence map representation images.

In some examples, a processor (e.g., of radiotherapy system 100) may apply image registration to register real fluence map representation training images to a training collection of projection images. This may create a one-to-one corresponding relationship between projection images at different angles (e.g., beam angles, gantry angles, etc.) and fluence map representation images at each of the different angles in the training data. This relationship may be referred to as paired or a pair of projection images and fluence map representation images.

In some implementations, CycleGAN 1631 may be implemented to generate a collection of fluence map representation images in accordance with an objective function that includes an adversarial loss term and a cycle consistency loss term. The CycleGAN network has two separate adversarial losses. Similar to the conditional GAN, the mapping G:X→Y and its associated discriminator $D_Y$ gives loss represented by:

$$\mathcal{L}_{GAN}(G,D_y) = \mathbb{E}_{y \sim p_{data}(y)}[\log(D_y)] + \mathbb{E}_{x \sim p_{data}(x)}[\log(1 - D_y(G(x)))] \quad \text{(Equation 12)}$$

With the CycleGAN, a network's forward cycle-consistency x→G(x)→F(G(x))≈x and the network's backward cycle-consistency y→F(y)→G(F(y))≈y. The adversarial losses in the network (e.g., using first/second generator models 1635/1637 and first/second discriminator models 1639A/1639B) are captured in the cycle-consistency losses as the L1 norms, $$\mathcal{L}_{cyc}(G,F) = \mathbb{E}_{x \sim p_{data}(x)}[\|F(G(x)) - x\|_1] + \mathbb{E}_{y \sim p_{data}(y)}[\|G(F(y)) - y\|_1] \quad \text{(Equation 13)}$$

Additionally, the identity loss regularizes the generator to be near an identity mapping when real samples of the target domain Y are input:

$$\mathcal{L}_{identity}(G,F) = \mathbb{E}_{y \sim p_{data}(y)}[\|G(y) - y\|_1] + \mathbb{E}_{x \sim p_{data}(x)}[\|F(x) - x\|_1] \quad \text{(Equation 14)}$$

Thus, the full loss function for the cycle-consistent GAN is $$\mathcal{L}(G,f,D_X,D_Y) = \mathcal{L}_{GAN}(G,D_Y) + \mathcal{L}_{GAN}(F,D_X) + \lambda_{cyc} \mathcal{L}_{cyc}(G,F) + \lambda_{identity} \mathcal{L}_{identity}(G,F) \quad \text{(Equation 15)}$$

where $D_X$ is the first discriminator model which determines whether one image is a true collection of fluence map representation images or a synthetic collection of fluence map representation images. $D_Y$ is the second discriminator model which determines whether one image is a true collection of projection images or a synthetic collection of projection images.

The preceding examples provide an example of how a GAN, a conditional GAN, or CycleGAN may be trained based on a collection of fluence map representation images and collection of projection image pairs, specifically from image data in 2D or 3D image slices in multiple parallel or sequential paths. It will be understood that the GAN, conditional GAN, or CycleGAN may process other forms of image data (e.g., 3D, or other multi-dimensional images) or representations of this data including in non-image format. Further, although only grayscale (including black and white) images are depicted by the accompanying drawings, it will be understood that other image formats and image data types may be generated and/or processed by the GAN.

FIG. 17 illustrates an example flowchart 1700 of a method for training a neural network model, such as a model that will be trained for generating a fluence map using the techniques and constraints discussed above. It will be apparent that additional operations, or a variation in the sequence of operations, may be implemented within this method.

At operation 1710, operations are performed to obtain training anatomy projection images, and at operation 1720, operations are performed to obtain training fluence map projection images. In this training scenario of flowchart 1700, pairs of anatomy projection images and fluence maps may be obtained from a plurality of human subjects, such that each corresponding pair of projection images and fluence maps is provided from a same human subject. Further, the corresponding pairs of the anatomy projection images and the fluence maps used for training the neural network model may be obtained for each beam angle of a radiotherapy treatment machine The operations 1710, 1720 may also involve other aspects of identifying, extracting, projecting, and modifying the projection images and the fluence maps, as suggested above.

The flowchart 1700 proceeds to operation 1730, to perform and supervise training of the model. In various examples, the model is implemented as a neural network, and the neural network model may be a generative model of a generative adversarial network (GAN). Such a GAN may include at least one generative model and at least one discriminative model, where the at least one generative model and the at least one discriminative model correspond to respective generative and discriminative convolutional neural networks. In still further examples, the GAN comprises a conditional adversarial network (cGAN) or a cycle-consistent generative adversarial network (CycleGAN). In operations 1740-1750 discussed below, operations are performed for GAN training; in operations 1755-1775, other operations are performed for CycleGAN training.

In an example, operations for GAN training (operations 1740-1750) involve using the GAN to train the generative model using a discriminative model. For instance, this may involve establishing the neural network parameter values using adversarial training between the discriminative model and the generative model, for learning the values by the generative model and the discriminative model. Such adversarial training may involve training the generative model to generate a first estimated fluence map at a first beam angle from a projection image that represents a view of a training subject anatomy from the first beam angle (operation 1740), training the discriminative model to classify the first estimated fluence map as an estimated or as a real training fluence map projection image (operation 1745), and using an output of the generative model for training the discriminative model and an output of the discriminative model for training the generative model (operation 1750).

In an example, operations for CycleGAN training (operations 1755-1775) involve using two sets of models in a GAN arrangement, involving a first discriminative model and a first generative model (trained with operations 1755, 1760, that correspond to operations 1740, 1745), and a second generative model and a second discriminative model (trained with operations 1765, 1770). Specifically, the second generative model is trained for processing, from a given pair of the pairs of anatomy projection images and fluence maps, a given fluence map at a given beam angle as an input, and generating an estimated anatomy projection image that represents a view of a subject anatomy from the given beam angle as an output. The second discriminative model is trained to classify the estimated anatomy projection image as an estimated or as a real anatomy projection image.

In an example, adversarial training for the first portion of the CycleGAN (the first generative and first discriminative models, corresponding to operations 1755, 1760) involves: obtaining a set of training anatomy projection images representing different views of a patient anatomy from prior treatments that are paired with a set of training fluence maps corresponding to each of the different views, each of the training fluence maps being aligned with a respective one of the training anatomy projection images; inputting the set of training anatomy projection images to the first generative model; and outputting a set of estimated fluence maps from the first generative model; inputting the set of estimated fluence maps to the first discriminative model, and classifying the set of estimated fluence maps with the first discriminative model as an estimated or as a real set of fluence maps; and inputting the set of fluence maps to the second generative model, and generating a set of estimated anatomy projection images, to calculate the cycle-consistency losses. In an example, adversarial training for the second portion of the CycleGAN (the second generative and second discriminative models, corresponding to operations 1765 and 1770) involves: inputting the set of training fluence maps corresponding to each of the different views to the second generative model, and outputting a set of generated anatomy projection images from the second generative model; inputting the set of generated anatomy projection images to the second discriminative model, and classifying the set of generated anatomy projection images as an estimated or real set of anatomy projection images; and inputting the set of anatomy projection images to the first generative model to generate a set of estimated fluence maps to calculate the cycle-consistency losses. From this adversarial training, cycle-consistency losses may be calculated and considered, to improve the training of the first generative model and the CycleGAN overall (operation 1775).

The flowchart 1700 concludes at operation 1780 with providing trained generative model (from the GAN, Cycle-GAN, or other training arrangement) for use with patient anatomy projection image(s), and in the radiology treatment planning processes described herein.

FIG. 18 illustrates an example of a method in a flowchart 1800 for using a trained neural network model, for determining a fluence map, based on the techniques discussed above. Additional operations, or a variation in the sequence of operations, may be implemented within this method, particularly when implemented as part of radiotherapy planning or treatment operations.

The flowchart 1800 begins with operation 1810, to obtain a three-dimensional set of image data corresponding to a subject of radiotherapy treatment. For instance, this may be performed by obtaining data from the use of imaging modalities (e.g., CT, MRI) that image a subject patient. The flowchart 1800 continues with operation 1820, to obtain the radiotherapy treatment constraints for the subject. For instance, this may be defined with the definition of target dose areas, organ at risk areas, as part of a radiotherapy treatment planning process. The flowchart 1800 continues with operation 1830, to generate three-dimensional image data indicating radiotherapy treatment constraints (e.g., the target dose areas, organ at risk areas). In an example, the input data provided with a trained model, referenced in operation 1860, below, is image data that indicates one or more target dose areas and one or more organs-at-risk areas in the anatomy of the subject.

The flowchart 1800 continues with operations to perform forward projection on three-dimensional image data (at operation 1840) and generate a projection image of the subject anatomy for each radiotherapy beam angle (at operation 1850). In an example, each anatomy projection image provides a view of the subject from a respective beam angle of the radiotherapy treatment, such as angles that correspond to each gantry angle used by a radiotherapy treatment machine.

The flowchart 1800 continues at operation 1860 with the use of a trained neural network model (e.g., trained according to the method indicated in flowchart 1700) to generate one or more fluence maps. In an example, the neural network model is trained with corresponding pairs of anatomy projection images and fluence maps provided from among multiple human subjects (e.g., as discussed with reference to FIG. 17). The flowchart 1800 concludes at operation 1870 with the production of a three-dimensional fluence map representation, such as provided from generation of multiple two-dimensional fluence maps generated by the trained model. In an example, the generated (estimated) fluence maps and the training of the model is provided for each radiotherapy beam angle used in radiotherapy treatment.

FIG. 19 provides a flowchart 1900 illustrating overall example operations of a processing system (e.g., the image processing device 112 or other computing system) coordinating a radiotherapy treatment and planning method, according to various examples. As discussed above, additional operations, or a variation in the sequence of operations, may be implemented within this method, particularly when implemented as part of radiotherapy planning or treatment operations.

At operation 1910, the method begins by obtaining three-dimensional image data, including radiotherapy constraints, that correspond to a subject for radiotherapy treatment. As indicated above, such image data may indicate one or more target dose areas and one or more organs-at-risk areas in the anatomy of the subject, and such image data may be converted or generated into projections in order for further processing.

At operation 1920, a trained neural network model is used to generate estimated fluence map representations (fluence maps). For instance, each of the estimated fluence maps may indicate a fluence distribution of the radiotherapy treatment at a respective beam angle. In a specific example, each of the estimated fluence maps is a two-dimensional array of beamlet weights normal to a respective beam direction, for beam angles of a radiotherapy treatment that correspond to gantry angles of a radiotherapy treatment machine At operation 1930, the fluence distribution is optimized based on the estimated fluence map representation. For instance, such optimization may involve performing numerical optimization with the estimated fluence maps being provided as input to the optimization, where the optimization incorporates radiotherapy treatment constraints to produce a pareto-optimal fluence plan used in the radiotherapy treatment plan for the subject.

At operation 1940, a set of initial control points is generated for radiotherapy beams based on the fluence distribution. In an example, this set of initial control points may be generated from performing arc sequencing based on the pareto-optimal fluence plan, to generate a set of initial control points corresponding to each of multiple radiotherapy beams. At operation 1950, a set of final control points is generated for the radiotherapy beams based on the initial control points. In an example, this set of final control points may be generated from performing direct aperture optimization, to generate a set of final control points corresponding to each of the multiple radiotherapy beams.

At operation 1960, radiotherapy is delivered with the radiotherapy beams based on final control points. In an example, the radiotherapy treatment is provided as a volume modulated arc therapy (VMAT) radiotherapy performed by a radiotherapy treatment machine, and the multiple radiotherapy beams are shaped to achieve a modulated coverage of the target dose areas from among multiple beam angles, to deliver a prescribed radiation dose. It will be apparent that other methods and optimizations of radiotherapy treatment may also be used.

Figure 20:
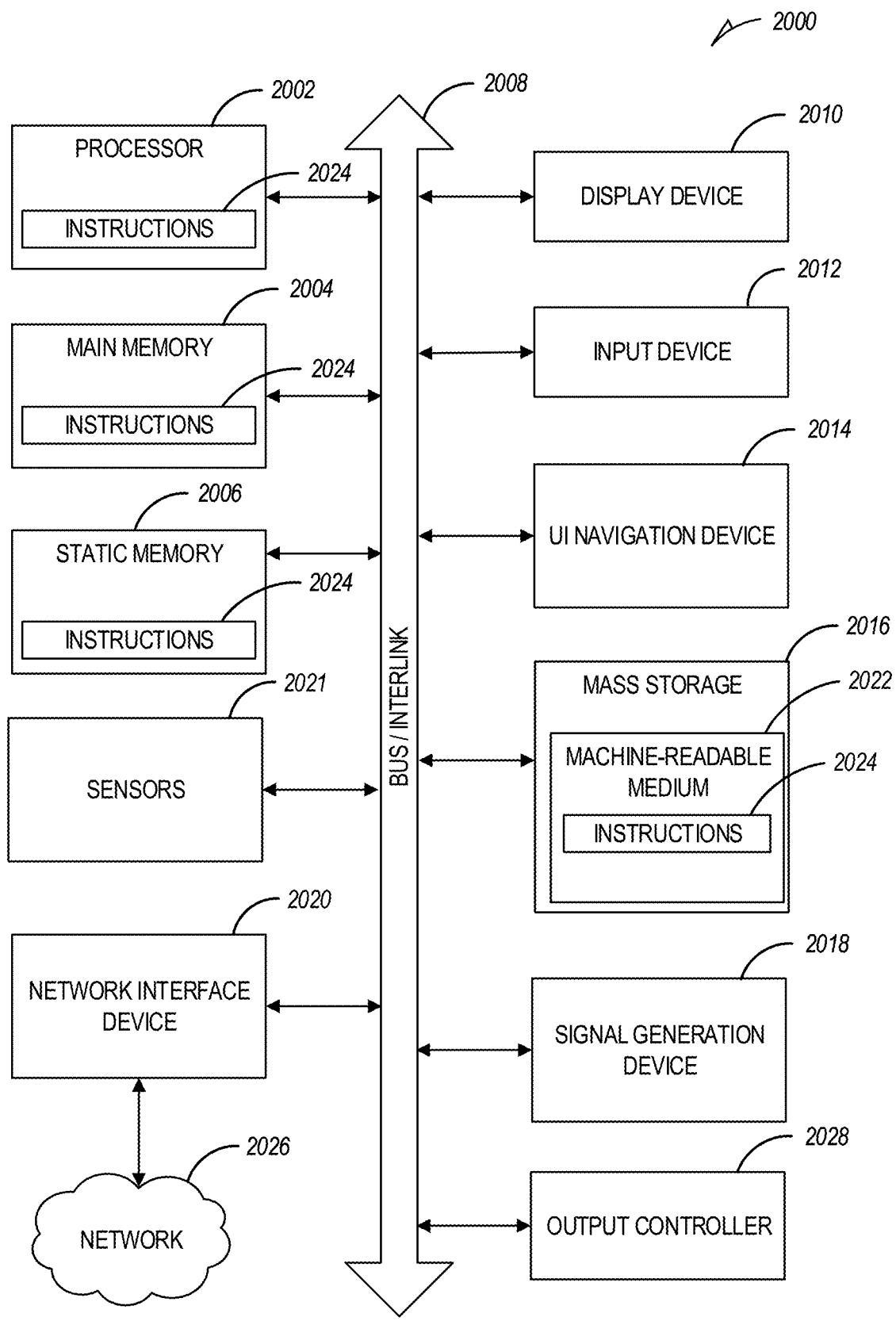
FIG. 20 illustrates an exemplary block diagram of a machine on which one or more of the methods as discussed herein can be implemented.

FIG. 20 illustrates a block diagram of an example of a machine 2000 on which one or more of the methods as discussed herein can be implemented. In one or more examples, one or more items of the image processing device 112 can be implemented by the machine 2000. In alternative examples, the machine 2000 operates as a standalone device or may be connected (e.g., networked) to other machines. In one or more examples, the image processing device 112 can include one or more of the items of the machine 2000. In a networked deployment, the machine 2000 may operate in the capacity of a server or a client machine in server-client network environment, or as a peer machine in a peer-to-peer (or distributed) network environment. The machine may be a personal computer (PC), server, a tablet, smartphone, a web appliance, edge computing device, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 2000 includes processing circuitry or processor 2002 (e.g., a CPU, a graphics processing unit (GPU), an ASIC, circuitry, such as one or more transistors, resistors, capacitors, inductors, diodes, logic gates, multiplexers, buffers, modulators, demodulators, radios (e.g., transmit or receive radios or transceivers), sensors 2021 (e.g., a transducer that converts one form of energy (e.g., light, heat, electrical, mechanical, or other energy) to another form of energy), or the like, or a combination thereof), a main memory 2004 and a static memory 2006, which communicate with each other via a bus 2008. The machine 2000 (e.g., computer system) may further include a video display device 2010 (e.g., a liquid crystal display (LCD) or a cathode ray tube (CRT)). The machine 2000 also includes an alphanumeric input device 2012 (e.g., a keyboard), a user interface (UI) navigation device 2014 (e.g., a mouse), a disk drive or mass storage unit 2016, a signal generation device 2018 (e.g., a speaker), and a network interface device 2020.

The disk drive unit 2016 includes a machine-readable medium 2022 on which is stored one or more sets of instructions and data structures (e.g., software) 2024 embodying or utilized by any one or more of the methodologies or functions described herein. The instructions 2024 may also reside, completely or at least partially, within the main memory 2004 and/or within the processor 2002 during execution thereof by the machine 2000, the main memory 2004 and the processor 2002 also constituting machine-readable media.

The machine 2000 as illustrated includes an output controller 2028. The output controller 2028 manages data flow to/from the machine 2000. The output controller 2028 is sometimes called a device controller, with software that directly interacts with the output controller 2028 being called a device driver.

While the machine-readable medium 2022 is shown in an example to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 2024 may further be transmitted or received over a communications network 2026 using a transmission medium. The instructions 2024 may be transmitted using the network interface device 2020 and any one of a number of well-known transfer protocols (e.g., HTTP). Examples of communication networks include a LAN, a WAN, the Internet, mobile telephone networks, Plain Old Telephone (POTS) networks, and wireless data networks (e.g., Wi-Fi and 4G/5G data networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer-readable storage medium is coupled to a computer system bus to be accessible by the processor and other parts of the OIS.

In an embodiment, the computer-readable storage medium may have encoded a data structure for treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A computer-implemented method for generating fluence maps used in a radiotherapy treatment plan, the method comprising:
    obtaining a three-dimensional set of image data corresponding to a subject of radiotherapy treatment, the image data indicating one or more target dose areas and one or more organs-at-risk areas in an anatomy of the subject;
    generating anatomy projection images from the image data, each image of the anatomy projection images providing a view of the subject from a respective beam angle of the radiotherapy treatment; and
    using a trained neural network model to generate estimated fluence maps based on the anatomy projection images, each of the estimated fluence maps indicating a fluence distribution of the radiotherapy treatment at a respective beam angle,
    wherein the neural network model is a trained generative model produced from training in a generative adversarial network (GAN) that includes at least one generative model and at least one discriminative model,
    wherein the neural network model is trained in the GAN with corresponding pairs of training anatomy projection images and training fluence maps, and
    wherein training of the at least one generative model of the GAN is based on generating synthetic fluence maps from the training anatomy projection images,
    wherein training of the at least one discriminative model of the GAN is based on discriminating the synthetic fluence maps from the training fluence maps, and
    wherein neural network parameter values learned by the at least one generative model of the GAN and the at least one discriminative model of the GAN are established from adversarial training.

2. The method of claim 1, wherein each of the estimated fluence maps is a two-dimensional array of beamlet weights normal to a respective beam direction, and wherein beam angles of the radiotherapy treatment correspond to gantry angles of a radiotherapy treatment machine.

3. The method of claim 2, wherein obtaining the three-dimensional set of image data corresponding to the subject includes obtaining image data for each gantry angle of the radiotherapy treatment machine, and wherein each generated anatomy projection image represents a view of the anatomy of the subject from a given gantry angle used to provide treatment with a given radiotherapy beam.

4. The method of claim 1, further comprising:
    using the estimated fluence maps to determine radiation doses in the radiotherapy treatment plan, wherein the radiotherapy treatment comprises a volume modulated arc therapy (VMAT) radiotherapy performed by a radiotherapy treatment machine, wherein multiple radiotherapy beams are shaped to achieve a modulated dose for target areas, from among multiple beam angles, to deliver a prescribed radiation dose.

5. The method of claim 1, wherein each image of the anatomy projection images is generated by forward projection of the three-dimensional set of image data from respective angles of multiple beam angles.

6. The method of claim 1, wherein training the neural network model uses pairs of anatomy projection images and fluence maps from a plurality of human subjects, wherein each individual pair is provided from a same human subject, and wherein the neural network model is trained with operations comprising:
    obtaining multiple sets of training anatomy projection images, each set of the training anatomy projection images indicating one or more target dose areas and one or more organs-at-risk areas in the anatomy of a respective human subject of the plurality of human subjects;
    obtaining multiple sets of training fluence maps corresponding to the training anatomy projection images, each set of the training fluence maps indicating a fluence distribution for the respective human subject of the plurality of human subjects; and
    training the neural network model based on the training anatomy projection images that correspond to the training fluence maps.

7. The method of claim 6, wherein the corresponding pairs of the anatomy projection images and the fluence maps used for training the neural network model are obtained for each beam angle of a radiotherapy treatment machine.

8. The method of claim 6, wherein the at least one generative model and the at least one discriminative model of the GAN correspond to respective generative and discriminative convolutional neural networks.

9. The method of claim 8, wherein the GAN comprises a conditional adversarial network (cGAN) or a cycle-consistent generative adversarial network (CycleGAN).

10. The method of claim 8,
    wherein the adversarial training comprises:
        training the at least one generative model to generate a first estimated fluence map at a first beam angle from a projection image that represents a view of the anatomy of the respective human subject from the first beam angle; and
        training the at least one discriminative model to classify the first estimated fluence map as a generated or as a real training fluence map projection image; and
    wherein an output of the at least one generative model is used for training the at least one discriminative model and an output of the at least one discriminative model is used for training the at least one generative model.

11. The method of claim 8, wherein the GAN is a cycle-consistent generative adversarial network (CycleGAN) comprising the at least one generative model and the at least one discriminative model, wherein the at least one generative model comprises a first generative model and the at least one discriminative model comprises a first discriminative model, wherein the CycleGAN further comprises:
a second generative model trained to:
process, from a given pair of the pairs of anatomy projection images and fluence maps, a given fluence map at a given beam angle as an input; and
generate an estimated anatomy projection image that represents a view of the anatomy of the respective human subject from the given beam angle as an output; and
a second discriminative model trained to classify the estimated anatomy projection image as a generated or as a real anatomy projection image.

12. The method of claim 11, wherein the CycleGAN comprises a first portion to train the first generative model, the first portion being trained to:
obtain a set of training anatomy projection images representing different views of a patient anatomy from prior treatments that are paired with a set of training fluence maps corresponding to each of the different views, each of the training fluence maps being aligned with a respective one of the training anatomy projection images;
input the set of training anatomy projection images to the first generative model, and output a set of estimated fluence maps from the first generative model;
input the set of estimated fluence maps to the first discriminative model, and classify the set of estimated fluence maps with the first discriminative model as a generated or as a real set of fluence maps; and
input the set of estimated fluence maps to the second generative model, and generate a set of estimated anatomy projection images, to calculate cycle-consistency losses.

13. The method of claim 12, wherein the CycleGAN comprises a second portion that is trained to:
input the set of training fluence maps corresponding to each of the different views to the second generative model, and output a set of generated anatomy projection images from the second generative model;
input the set of generated anatomy projection images to the second discriminative model, and classify the set of generated anatomy projection images as a generated or as a real set of anatomy projection images; and
input the set of generated anatomy projection images to the first generative model to generate a set of estimated fluence maps to calculate the cycle-consistency losses.

14. The method of claim 12, wherein:
the cycle-consistency losses are generated based on:
a) a comparison of the set of generated anatomy projection images with the set of training anatomy projection images, and
b) a comparison of the set of generated fluence maps with the set of training fluence maps;
wherein the first generative model is trained to minimize a first loss term that represents an expectation of a difference between a plurality of the estimated fluence maps and respectively paired training fluence maps; and
wherein the second generative model is trained to minimize a second loss term that represents an expectation of difference between a plurality of the estimated anatomy projection images and respectively paired training anatomy projection images.

15. The method of claim 1, further comprising:
generating a set of estimated fluence maps using the neural network model; and
performing numerical optimization with the estimated fluence maps as input to the optimization, wherein the optimization incorporates radiotherapy treatment constraints to produce a pareto-optimal fluence plan used in the radiotherapy treatment plan for the subject.

16. The method of claim 15, further comprising:
performing arc sequencing based on the pareto-optimal fluence plan, to generate a set of initial control points corresponding to each of multiple radiotherapy beams; and
performing direct aperture optimization, to generate a set of final control points corresponding to each of the multiple radiotherapy beams.

17. The method of claim 16, wherein the radiotherapy treatment comprises a volume modulated arc therapy (VMAT) radiotherapy performed by a radiotherapy treatment machine, and wherein the arc sequencing based on the pareto-optimal fluence plan is performed such that the multiple radiotherapy beams are shaped to achieve a modulated coverage of the one or more target dose areas, from among multiple beam angles, to deliver a prescribed radiation dose.

18. The method of claim 16, further comprising:
performing the radiotherapy treatment, using the set of final control points, wherein the set of final control points are used to control multi-leaf collimator (MLC) leaf positions of a radiotherapy treatment machine at a given gantry angle corresponding to a given beam angle.

19. The method of claim 1, further comprising:
comparing a fluence map produced from the neural network model in response to an input set of anatomy projection images, with a fluence map produced from another source.

20. The method of claim 1, wherein the adversarial training comprises:
training the at least one generative model to generate a first estimated fluence map at a first beam angle from a projection image that represents a view of anatomy from the first beam angle; and
training the at least one discriminative model to classify the first estimated fluence map as a generated or as a real training fluence map projection image;
wherein an output of the at least one generative model is used for training the at least one discriminative model and an output of the at least one discriminative model is used for training the at least one generative model.

21. The method of claim 1, wherein the GAN comprises a conditional adversarial network (cGAN),
wherein training of the at least one generative model of the cGAN is based on generating the training fluence maps from the training anatomy projection images and wherein training of the at least one discriminative model of the cGAN is based on discriminating data from the training fluence maps, and
wherein the training in the cGAN is conditioned by at least one radiotherapy treatment target area or at least one organs at risk area defined in the training anatomy projection images.

22. A system for generating fluence maps used in a radiotherapy treatment plan, the system comprising:

one or more memory devices to store a three-dimensional set of image data corresponding to a subject of radiotherapy treatment, the image data indicating one or more target dose areas and one or more organs-at-risk areas in an anatomy of the subject; and one or more processors configured to perform operations comprising:

obtaining anatomy projection images from the image data, each image of the anatomy projection images providing a view of the subject from a respective beam angle of the radiotherapy treatment; and executing a trained neural network model to generate computer-estimated fluence maps based on input of the anatomy projection images, each of the estimated fluence maps indicating a fluence distribution of the radiotherapy treatment at a respective beam angle, wherein the neural network model is a generative model produced from training in a generative adversarial network (GAN) that includes at least one generative model and at least one discriminative model, wherein the neural network model is trained in the GAN with corresponding pairs of training anatomy projection images and training fluence maps, and wherein training of the at least one generative model of the GAN is based on generating synthetic fluence maps from the training anatomy projection images, wherein training of the at least one discriminative model of the GAN is based on discriminating the synthetic fluence maps from the training fluence maps, and wherein neural network parameter values learned by the at least one generative model of the GAN and the at least one discriminative model of the GAN are established from adversarial training.

23. The system of claim 22, the one or more processors further configured to perform operations comprising:

generating a set of estimated fluence maps using the neural network model; and performing numerical optimization with the estimated fluence maps as input to the optimization, wherein the optimization incorporates radiotherapy treatment constraints to produce a pareto-optimal fluence plan used in the radiotherapy treatment plan for the subject;

wherein each of the estimated fluence maps is a two-dimensional array of beamlet weights normal to a respective beam direction, and wherein beam angles of the radiotherapy treatment correspond to gantry angles of a radiotherapy treatment machine.

24. The system of claim 23, the one or more processors further configured to perform operations comprising:

performing arc sequencing based on the pareto-optimized fluence plan, to generate a set of initial control points corresponding to each of multiple radiotherapy beams; and performing direct aperture optimization, to generate a set of final control points corresponding to each of the multiple radiotherapy beams.

25. The system of claim 22, the one or more processors further configured to perform operations comprising:

using the estimated fluence maps to determine radiation doses in the radiotherapy treatment plan, wherein the radiotherapy treatment comprises a volume modulated arc therapy (VMAT) radiotherapy performed by a radiotherapy treatment machine, wherein multiple radiotherapy beams are shaped to achieve a modulated dose for target areas, from among multiple beam angles, to deliver a prescribed radiation dose.

26. The system of claim 25, wherein training the neural network model uses pairs of anatomy projection images and fluence maps from a plurality of human subjects, wherein each individual pair is provided from a same human subject, and wherein the neural network model is trained with operations comprising:

obtaining multiple sets of training anatomy projection images, each set of the training anatomy projection images indicating one or more target dose areas and one or more organs-at-risk areas in the anatomy of a respective human subject of the plurality of human subjects;

obtaining multiple sets of training fluence maps corresponding to the training anatomy projection images, each set of the training fluence maps indicating a fluence distribution for the respective human subject of the plurality of human subjects; and training the neural network model based on the training anatomy projection images that correspond to the training fluence maps;

wherein the at least one generative model and the at least one discriminative model correspond to respective generative and discriminative convolutional neural networks.

27. The system of claim 22, wherein the adversarial training comprises:

training the at least one generative model to generate a first estimated fluence map at a first beam angle from a projection image that represents a view of anatomy from the first beam angle; and training the at least one discriminative model to classify the first estimated fluence map as a generated or as a real training fluence map projection image;

wherein an output of the at least one generative model is used for training the at least one discriminative model and an output of the at least one discriminative model is used for training the at least one generative model.

28. The system of claim 22, wherein the GAN comprises a conditional adversarial network (cGAN), wherein training of the at least one generative model of the cGAN is based on generating the training fluence maps from the training anatomy projection images and wherein training of the at least one discriminative model of the cGAN is based on discriminating data from the training fluence maps, and wherein the training in the cGAN is conditioned by at least one radiotherapy treatment target area or at least one organs at risk area defined in the training anatomy projection images.

29. A non-transitory computer-readable storage medium comprising computer-readable instructions for generating fluence maps used in a radiotherapy treatment plan, the instructions performing operations comprising:

identifying a three-dimensional set of image data corresponding to a subject of radiotherapy treatment, the image data indicating one or more target dose areas and one or more organs-at-risk areas in an anatomy of the subject;

generating anatomy projection images from the image data, each image of the anatomy projection images providing a view of the subject from a respective beam angle of the radiotherapy treatment; and using a trained neural network model to generate computer-estimated fluence maps based on input of the anatomy projection images, each of the estimated fluence maps indicating a fluence distribution of the radiotherapy treatment at a respective beam angle, wherein the neural network model is a generative model produced from training in a generative adversarial network (GAN) that includes at least one generative model and at least one discriminative model, wherein the neural network model is trained in the GAN with corresponding pairs of training anatomy projection training images and training fluence maps, and wherein training of the at least one generative model of the GAN is based on generating synthetic fluence maps from the training anatomy projection images, wherein training of the at least one discriminative model of the GAN is based on discriminating the synthetic fluence maps from the training fluence maps, and wherein neural network parameter values learned by the at least one generative model of the GAN and the at least one discriminative model of the GAN are established from adversarial training.

30. The computer-readable storage medium of claim 29, the instructions further performing operations comprising:
generating a set of estimated fluence maps using the neural network model; and
performing numerical optimization with the estimated fluence maps as input to the optimization, wherein the optimization incorporates radiotherapy treatment constraints to produce a pareto-optimal fluence plan used in the radiotherapy treatment plan for the subject;
wherein each of the estimated fluence maps is a two-dimensional array of beamlet weights normal to a respective beam direction, and wherein beam angles of the radiotherapy treatment correspond to gantry angles of a radiotherapy treatment machine.

31. The computer-readable storage medium of claim 30, the instructions further performing operations comprising:
performing arc sequencing based on the pareto-optimal fluence plan, to generate a set of initial control points corresponding to each of multiple radiotherapy beams; and
performing direct aperture optimization, to generate a set of final control points corresponding to each of the multiple radiotherapy beams.

32. The computer-readable storage medium of claim 29, the instructions further performing operations comprising:
using the estimated fluence maps to determine radiation doses in the radiotherapy treatment plan, wherein the radiotherapy treatment comprises a volume modulated arc therapy (VMAT) radiotherapy performed by a radiotherapy treatment machine, wherein multiple radiotherapy beams are shaped to achieve a modulated dose for target areas, from among multiple beam angles, to deliver a prescribed radiation dose.

33. The computer-readable storage medium of claim 29, wherein training the neural network model uses pairs of anatomy projection images and fluence maps from a plurality of human subjects, wherein each individual pair is provided from a same human subject, and wherein the neural network model is trained with operations comprising:
obtaining multiple sets of training anatomy projection images, each set of the training anatomy projection images indicating one or more target dose areas and one or more organs-at-risk areas in the anatomy of a respective human subject of the plurality of human subjects;
obtaining multiple sets of training fluence maps corresponding to the training anatomy projection images, each set of the training fluence maps indicating a fluence distribution for the respective human subject of the plurality of human subjects; and
training the neural network model based on the training anatomy projection images that correspond to the training fluence maps;
wherein the at least one generative model and the at least one discriminative model correspond to respective generative and discriminative convolutional neural networks.

34. The computer-readable storage medium of claim 29, wherein the adversarial training comprises:
training the at least one generative model to generate a first estimated fluence map at a first beam angle from a projection image that represents a view of anatomy from the first beam angle; and
training the at least one discriminative model to classify the first estimated fluence map as a generated or as a real training fluence map projection image;
wherein an output of the at least one generative model is used for training the at least one discriminative model and an output of the at least one discriminative model is used for training the at least one generative model.

35. The computer-readable storage medium of claim 29, wherein the GAN comprises a conditional adversarial network (cGAN),
wherein training of the at least one generative model of the cGAN is based on generating the training fluence maps from the training anatomy projection images and wherein training of the at least one discriminative model of the cGAN is based on discriminating data from the training fluence maps, and
wherein the training in the cGAN is conditioned by at least one radiotherapy treatment target area or at least one organs at risk area defined in the training anatomy projection images.

* * * * *